(12) United States Patent
Neuhauser et al.

(10) Patent No.: US 11,741,431 B2
(45) Date of Patent: Aug. 29, 2023

(54) METHODS AND SYSTEMS FOR COMPLIANCE CONFIRMATION AND INCENTIVES

(71) Applicant: The Nielsen Company (US), LLC, New York, NY (US)

(72) Inventors: Alan R. Neuhauser, Silver Spring, MD (US); Jack C. Crystal, Owings Mills, MD (US); Jack K. Zhang, Ijamsville, MD (US); Eugene L. Flanagan, Wilton, CT (US)

(73) Assignee: The Nielsen Company (US), LLC, New York, NY (US)

( * ) Notice: Subject to any disclaimer, the term of this patent is extended or adjusted under 35 U.S.C. 154(b) by 880 days.

(21) Appl. No.: 16/544,879

(22) Filed: Aug. 19, 2019

(65) Prior Publication Data

US 2019/0371462 A1 Dec. 5, 2019

Related U.S. Application Data

(63) Continuation of application No. 15/331,510, filed on Oct. 21, 2016, now Pat. No. 10,387,618, which is a
(Continued)

(51) Int. Cl.
G06Q 30/0201 (2023.01)
G06Q 30/018 (2023.01)
(Continued)

(52) U.S. Cl.
CPC ......... *G06Q 10/101* (2013.01); *A61B 3/1216* (2013.01); *A61B 3/14* (2013.01);
(Continued)

(58) Field of Classification Search
None
See application file for complete search history.

(56) References Cited

U.S. PATENT DOCUMENTS 4,107,734 A 8/1978 Percy et al.
4,107,735 A 8/1978 Frohbach
(Continued)

FOREIGN PATENT DOCUMENTS

CA 2033558 11/1996
CA 2658979 1/2008
(Continued)

OTHER PUBLICATIONS

C. Ben Abdelkader, R. Cutler and L. Davis, "Stride and cadence as a biometric in automatic person identification and verification," Proceedings of Fifth IEEE International Conference on Automatic Face Gesture Recognition, Washington, DC, USA, 2002, pp. 372-377, doi: 10.1109/AFGR.2002.1004182. (Year: 2002).*
(Continued)

*Primary Examiner* — Andrew B Whitaker
(74) *Attorney, Agent, or Firm* — HANLEY, FLIGHT & ZIMMERMAN, LLC

(57) ABSTRACT

Example methods, apparatus, and articles of manufacture for monitoring use by a user of a portable research device in accordance with at least one predetermined use criterion are disclosed. The disclosed examples include passively gathering data for assessing an identity of a user of the portable research device, processing the passively gathered data to produce assessment data indicating a possibility that the user is not a predetermined correct user of the portable research device, based on the assessment data, displaying a message to the user requesting a response from which the user's identity may be determined, and processing a response to the message to produce data indicating whether the user is the predetermined correct user.

20 Claims, 14 Drawing Sheets

Related U.S. Application Data continuation of application No. 11/777,051, filed on Jul. 12, 2007, now Pat. No. 9,489,640.

(60) Provisional application No. 60/831,744, filed on Jul. 12, 2006.

(51) Int. Cl.

| | | |
|---|---|---|
| *G06Q 10/101* | (2023.01) | |
| *G16H 40/67* | (2018.01) | |
| *G16H 40/20* | (2018.01) | |
| *G16H 10/60* | (2018.01) | |
| *G16H 30/20* | (2018.01) | |
| *G16H 40/63* | (2018.01) | |
| *G06Q 10/00* | (2023.01) | |
| *A61B 3/12* | (2006.01) | |
| *A61B 3/14* | (2006.01) | |
| *A61B 5/00* | (2006.01) | |
| *A61B 5/0205* | (2006.01) | |
| *A61B 5/1172* | (2016.01) | |
| *A61B 5/1171* | (2016.01) | |
| *A61B 7/00* | (2006.01) | |
| *A61B 7/02* | (2006.01) | |
| *G06Q 30/0203* | (2023.01) | |
| *A61B 5/024* | (2006.01) | |
| *A61B 5/08* | (2006.01) | |

(52) U.S. Cl.
CPC .......... *A61B 5/0077* (2013.01); *A61B 5/0205* (2013.01); *A61B 5/1172* (2013.01); *A61B 5/1176* (2013.01); *A61B 5/489* (2013.01); *A61B 5/4833* (2013.01); *A61B 5/6898* (2013.01); *A61B 7/003* (2013.01); *A61B 7/008* (2013.01); *A61B 7/02* (2013.01); *G06Q 10/00* (2013.01); *G06Q 30/018* (2013.01); *G06Q 30/0201* (2013.01); *G16H 10/60* (2018.01); *G16H 30/20* (2018.01); *G16H 40/20* (2018.01); *G16H 40/63* (2018.01); *G16H 40/67* (2018.01); *A61B 5/02438* (2013.01); *A61B 5/0816* (2013.01); *A61B 2503/12* (2013.01); *G06Q 30/0203* (2013.01)

(56) References Cited

U.S. PATENT DOCUMENTS

| | | | |
|---|---|---|---|
| 4,258,386 A | | 3/1981 | Cheung |
| 4,308,554 A | | 12/1981 | Percy et al. |
| 4,567,511 A | | 1/1986 | Smith et al. |
| 4,584,602 A | | 4/1986 | Nakagawa |
| 4,626,904 A | | 12/1986 | Lurie |
| 4,642,685 A | | 2/1987 | Roberts et al. |
| 4,646,145 A | | 2/1987 | Percy et al. |
| 4,652,915 A | | 3/1987 | Heller, III |
| 4,658,290 A | | 4/1987 | McKenna et al. |
| 4,695,879 A | | 9/1987 | Weinblatt |
| 4,697,209 A | | 9/1987 | Kiewit et al. |
| 4,718,106 A | | 1/1988 | Weinblatt |
| 4,779,198 A | | 10/1988 | Lurie |
| 4,803,625 A | | 2/1989 | Fu et al. |
| 4,907,079 A | | 3/1990 | Turner et al. |
| 4,912,552 A | | 3/1990 | Allison, III et al. |
| 4,955,070 A | | 9/1990 | Welsh et al. |
| 4,973,952 A | | 11/1990 | Malec et al. |
| 5,023,929 A | | 6/1991 | Call |
| 5,155,762 A | | 10/1992 | Croquet et al. |
| 5,331,544 A | * | 7/1994 | Lu .......................... G06Q 30/02 |
| | | | 705/7.29 |
| 5,382,970 A | | 1/1995 | Kiefl |
| 5,483,276 A | | 1/1996 | Brooks et al. |
| 5,579,124 A | | 11/1996 | Aijala et al. |
| 5,704,029 A | | 12/1997 | Wright, Jr. |
| 5,737,026 A | | 4/1998 | Lu et al. |
| 5,822,744 A | | 10/1998 | Kesel |
| 5,864,708 A | | 1/1999 | Croft et al. |
| 6,001,065 A | | 12/1999 | DeVito |
| 6,016,476 A | * | 1/2000 | Maes .................... G07F 7/1008 |
| | | | 705/26.1 |
| 6,026,387 A | | 2/2000 | Kesel |
| 6,035,177 A | | 3/2000 | Moses et al. |
| 6,271,631 B1 | | 8/2001 | Burrows |
| 6,294,999 B1 | | 9/2001 | Yarin et al. |
| 6,380,928 B1 | | 4/2002 | Todd |
| 6,456,981 B1 | | 9/2002 | Dejaeger et al. |
| 6,467,089 B1 | | 10/2002 | Aust et al. |
| 6,484,033 B2 | | 11/2002 | Murray |
| 6,524,239 B1 | * | 2/2003 | Reed .................... A61B 5/0002 |
| | | | 128/920 |
| 6,564,104 B2 | | 5/2003 | Nelson et al. |
| 6,572,560 B1 | | 6/2003 | Watrous et al. |
| 6,574,614 B1 | | 6/2003 | Kesel |
| 6,623,427 B2 | | 9/2003 | Mandigo |
| 6,623,428 B2 | | 9/2003 | Miller et al. |
| 6,647,548 B1 | | 11/2003 | Lu et al. |
| 6,661,438 B1 | | 12/2003 | Shiraishi et al. |
| 6,699,188 B2 | | 3/2004 | Wessel |
| 6,754,470 B2 | | 6/2004 | Hendrickson et al. |
| 6,757,719 B1 | | 6/2004 | Lightman et al. |
| 6,790,178 B1 | | 9/2004 | Mault et al. |
| 6,819,219 B1 | * | 11/2004 | Bolle ............... G06Q 20/40145 |
| | | | 340/5.82 |
| 6,893,396 B2 | | 5/2005 | Schulze et al. |
| 6,912,386 B1 | | 6/2005 | Himberg et al. |
| 6,963,848 B1 | | 11/2005 | Brinkerhoff |
| 6,968,564 B1 | | 11/2005 | Srinivasan |
| 7,020,082 B2 | | 3/2006 | Bhagavath et al. |
| 7,054,666 B2 | | 5/2006 | Shibuya |
| 7,065,351 B2 | | 6/2006 | Carter et al. |
| 7,139,916 B2 | | 11/2006 | Billingsley et al. |
| 7,162,202 B2 | | 1/2007 | Westman |
| 7,178,726 B2 | * | 2/2007 | Matsumoto ............ G06Q 30/02 |
| | | | 235/383 |
| 7,181,159 B2 | | 2/2007 | Breen |
| 7,263,086 B2 | | 8/2007 | Viikari et al. |
| 7,275,261 B2 | | 9/2007 | Kutaragi et al. |
| 7,363,214 B2 | | 4/2008 | Musgrove et al. |
| 7,376,430 B2 | | 5/2008 | Matsuda |
| 7,493,388 B2 | | 2/2009 | Wen et al. |
| 7,547,279 B2 | | 6/2009 | Kim et al. |
| 7,555,470 B2 | | 6/2009 | Brown |
| 7,593,719 B2 | | 9/2009 | Kim |
| 7,607,147 B1 | | 10/2009 | Lu et al. |
| 7,616,110 B2 | | 11/2009 | Crump et al. |
| 7,644,422 B2 | | 1/2010 | Lu et al. |
| 7,739,705 B2 | | 6/2010 | Lee et al. |
| 8,046,797 B2 | | 10/2011 | Bentolila et al. |
| 8,060,753 B2 | * | 11/2011 | King ..................... G06F 21/32 |
| | | | 713/169 |
| 8,073,707 B2 | * | 12/2011 | Teller .................... G16H 20/30 |
| 8,135,606 B2 | | 3/2012 | Dupree |
| 8,181,848 B2 | | 5/2012 | Olmsted et al. |
| 8,434,100 B2 | | 4/2013 | Wheeler et al. |
| 8,532,610 B2 | | 9/2013 | Manning et al. |
| 8,548,373 B2 | | 10/2013 | Peiffer et al. |
| 8,583,782 B2 | | 11/2013 | Park et al. |
| 8,601,163 B2 | | 12/2013 | Ramaswamy et al. |
| 8,650,586 B2 | | 2/2014 | Lee et al. |
| 8,732,738 B2 | | 5/2014 | Lu et al. |
| 8,826,317 B2 | | 9/2014 | Krug |
| 8,830,792 B2 | | 9/2014 | Taylor et al. |
| 9,094,710 B2 | | 7/2015 | Lee et al. |
| 9,106,347 B2 | | 8/2015 | Ramaswamy et al. |
| 9,191,581 B2 | | 11/2015 | Srinivasan et al. |
| 9,197,931 B2 | | 11/2015 | Krug |
| 9,209,917 B2 | | 12/2015 | Donald et al. |
| 9,326,034 B2 | | 4/2016 | Mears et al. |
| 9,332,363 B2 | | 5/2016 | Jain et al. |
| 9,489,640 B2 | | 11/2016 | Neuhauser et al. |
| 9,514,135 B2 | | 12/2016 | Fisch et al. |
| 9,794,619 B2 | | 10/2017 | Lee et al. |

(56) References Cited

U.S. PATENT DOCUMENTS

| | | |
|---|---|---|
| 10,387,618 B2 | 8/2019 | Neuhauser et al. |
| 2001/0000668 A1 | 5/2001 | Bodnar |
| 2001/0032115 A1 | 10/2001 | Goldstein |
| 2001/0037206 A1 | 11/2001 | Falk et al. |
| 2002/0010919 A1 | 1/2002 | Lu et al. |
| 2002/0019584 A1 | 2/2002 | Schulze et al. |
| 2002/0026348 A1 | 2/2002 | Fowler et al. |
| 2002/0039070 A1 | 4/2002 | Ververs et al. |
| 2002/0045519 A1 | 4/2002 | Watterson et al. |
| 2002/0056043 A1 | 5/2002 | Glass |
| 2002/0082771 A1 | 6/2002 | Anderson |
| 2002/0138848 A1 | 9/2002 | Alao et al. |
| 2002/0143563 A1 | 10/2002 | Hufford et al. |
| 2002/0143577 A1 | 10/2002 | Shiffman et al. |
| 2002/0181711 A1 | 12/2002 | Logan et al. |
| 2002/0188652 A1 | 12/2002 | Goldhaber et al. |
| 2002/0198762 A1 | 12/2002 | Donato |
| 2002/0198990 A1 | 12/2002 | Bradfield et al. |
| 2003/0006911 A1 | 1/2003 | Smith et al. |
| 2003/0032409 A1 | 2/2003 | Hutcheson et al. |
| 2003/0036683 A1 | 2/2003 | Kehr et al. |
| 2003/0046685 A1 | 3/2003 | Srinivasan et al. |
| 2003/0054866 A1 | 3/2003 | Byers et al. |
| 2003/0073922 A1 | 4/2003 | Miller et al. |
| 2003/0086341 A1 | 5/2003 | Wells et al. |
| 2003/0093783 A1 | 5/2003 | Nelson |
| 2003/0101451 A1 | 5/2003 | Bentolila et al. |
| 2003/0110485 A1 | 6/2003 | Lu et al. |
| 2003/0126250 A1 | 7/2003 | Jhanji |
| 2003/0131350 A1 | 7/2003 | Peiffer et al. |
| 2003/0170001 A1 | 9/2003 | Breen |
| 2003/0171833 A1 | 9/2003 | Crystal et al. |
| 2004/0005900 A1 | 1/2004 | Zilliacus |
| 2004/0006478 A1 | 1/2004 | Alpdemir et al. |
| 2004/0010418 A1 | 1/2004 | Buonocore et al. |
| 2004/0064319 A1 | 4/2004 | Neuhauser et al. |
| 2004/0068737 A1 | 4/2004 | Itoh et al. |
| 2004/0078214 A1 | 4/2004 | Speiser et al. |
| 2004/0095897 A1 | 5/2004 | Vafaei |
| 2004/0103139 A1 | 5/2004 | Hubbard et al. |
| 2004/0109061 A1 | 6/2004 | Walker et al. |
| 2004/0192299 A1 | 9/2004 | Wilson et al. |
| 2004/0203630 A1 | 10/2004 | Wang |
| 2004/0209595 A1 | 10/2004 | Bekanich |
| 2004/0235460 A1 | 11/2004 | Engstrom et al. |
| 2004/0243468 A1 | 12/2004 | Cohagan et al. |
| 2004/0252816 A1 | 12/2004 | Nicolas |
| 2004/0255322 A1 | 12/2004 | Meadows et al. |
| 2005/0096920 A1 | 5/2005 | Matz et al. |
| 2005/0120389 A1 | 6/2005 | Boss et al. |
| 2005/0144632 A1 | 6/2005 | Mears et al. |
| 2005/0172021 A1 | 8/2005 | Brown |
| 2005/0197988 A1 | 9/2005 | Bublitz |
| 2005/0203800 A1 | 9/2005 | Sweeney et al. |
| 2005/0213511 A1* | 9/2005 | Reece, Jr. ............ H04W 24/00 370/252 |
| 2005/0216509 A1* | 9/2005 | Kolessar .......... H04N 21/44204 |
| 2005/0228718 A1 | 10/2005 | Austin |
| 2005/0234309 A1 | 10/2005 | Klapper |
| 2005/0234774 A1 | 10/2005 | Dupree |
| 2005/0250470 A1 | 11/2005 | Wen et al. |
| 2005/0253683 A1* | 11/2005 | Lowe .................... G07C 9/257 340/5.61 |
| 2005/0268798 A1 | 12/2005 | Neuhauser et al. |
| 2005/0289582 A1 | 12/2005 | Tavares et al. |
| 2006/0036134 A1 | 2/2006 | Tarassenko et al. |
| 2006/0041657 A1 | 2/2006 | Wen et al. |
| 2006/0059364 A1 | 3/2006 | Fontijn |
| 2006/0095331 A1 | 5/2006 | O'Malley et al. |
| 2006/0101116 A1 | 5/2006 | Rittman et al. |
| 2006/0106875 A1 | 5/2006 | Terakawa et al. |
| 2006/0139150 A1 | 6/2006 | Brue |
| 2006/0154642 A1 | 7/2006 | Scannell, Jr. |
| 2006/0168613 A1 | 7/2006 | Wood et al. |
| 2006/0184493 A1 | 8/2006 | Shiffman et al. |
| 2006/0218034 A1 | 9/2006 | Kelly |
| 2006/0235764 A1 | 10/2006 | Bamborough et al. |
| 2006/0240877 A1 | 10/2006 | Filiba et al. |
| 2006/0293802 A1 | 12/2006 | Kitao et al. |
| 2006/0294108 A1 | 12/2006 | Adelson et al. |
| 2007/0064160 A1 | 3/2007 | Tanaka et al. |
| 2007/0136129 A1 | 6/2007 | Handley et al. |
| 2007/0138251 A1 | 6/2007 | Mattlin et al. |
| 2007/0208232 A1* | 9/2007 | Kovacs ................ A61B 5/1118 600/595 |
| 2007/0208233 A1* | 9/2007 | Kovacs ............. A61B 5/14551 600/323 |
| 2007/0288277 A1 | 12/2007 | Neuhauser et al. |
| 2007/0288476 A1 | 12/2007 | Flanagan, III et al. |
| 2007/0294057 A1 | 12/2007 | Crystal et al. |
| 2007/0294706 A1 | 12/2007 | Neuhauser et al. |
| 2008/0059988 A1 | 3/2008 | Lee et al. |
| 2008/0071786 A1 | 3/2008 | Swanburg et al. |
| 2008/0082995 A1 | 4/2008 | Tanaka et al. |
| 2008/0086533 A1 | 4/2008 | Neuhauser et al. |
| 2008/0091087 A1 | 4/2008 | Neuhauser et al. |
| 2008/0091451 A1 | 4/2008 | Crystal |
| 2008/0091762 A1 | 4/2008 | Neuhauser et al. |
| 2008/0109295 A1 | 5/2008 | McConochie et al. |
| 2008/0133291 A1 | 6/2008 | Nasser et al. |
| 2008/0204273 A1 | 8/2008 | Crystal et al. |
| 2009/0085873 A1 | 4/2009 | Betts et al. |
| 2009/0171767 A1 | 7/2009 | Kolessar |
| 2009/0193052 A1 | 7/2009 | FitzGerald et al. |
| 2010/0077420 A1 | 3/2010 | Nielsen et al. |
| 2010/0102981 A1 | 4/2010 | Nielsen et al. |
| 2010/0269127 A1 | 10/2010 | Krug |
| 2012/0011528 A1 | 1/2012 | Nielsen et al. |
| 2012/0155662 A1 | 6/2012 | Tawada |
| 2012/0173701 A1 | 7/2012 | Tenbrock |
| 2012/0245978 A1 | 9/2012 | Jain et al. |
| 2012/0278377 A1 | 11/2012 | Weissman et al. |
| 2013/0035979 A1 | 2/2013 | Tenbrock |
| 2013/0202128 A1 | 8/2013 | Jain et al. |
| 2014/0337873 A1 | 11/2014 | Krug |
| 2015/0222951 A1 | 8/2015 | Ramaswamy |
| 2015/0269824 A1 | 9/2015 | Zhang |

FOREIGN PATENT DOCUMENTS

| | | |
|---|---|---|
| CA | 2659240 | 1/2008 |
| CA | 2659244 | 1/2008 |
| CA | 2659277 | 1/2008 |
| CN | 1324193 | 11/2001 |
| CN | 1364392 | 8/2002 |
| CN | 1486576 | 3/2004 |
| CN | 1518391 | 8/2004 |
| CN | 1643886 | 7/2005 |
| CN | 1649426 | 8/2005 |
| CN | 1701335 | 11/2005 |
| CN | 1717694 | 1/2006 |
| JP | 2120987 | 5/1990 |
| JP | 2298185 | 12/1990 |
| JP | 3035407 | 2/1991 |
| JP | 3117075 | 5/1991 |
| JP | 5327638 | 12/1993 |
| JP | 7079206 | 3/1995 |
| JP | 11501177 | 1/1996 |
| JP | 0846587 | 2/1996 |
| JP | 8046588 | 2/1996 |
| JP | 9035067 | 2/1997 |
| JP | 9036822 | 2/1997 |
| JP | 9113367 | 5/1997 |
| JP | 9145362 | 6/1997 |
| JP | 9145368 | 6/1997 |
| JP | 10145823 | 5/1998 |
| JP | 10163992 | 6/1998 |
| JP | 11122203 | 4/1999 |
| JP | 11122204 | 4/1999 |
| JP | 11272287 | 10/1999 |
| JP | 11275032 | 10/1999 |
| JP | 11275608 | 10/1999 |
| JP | 11355228 | 12/1999 |
| JP | 2000092007 | 3/2000 |

(56) References Cited

FOREIGN PATENT DOCUMENTS

| | | |
|---|---|---|
| JP | 2000505618 | 5/2000 |
| JP | 2001502130 | 2/2001 |
| JP | 2001188703 | 7/2001 |
| JP | 2001324988 | 11/2001 |
| JP | 2001524776 | 12/2001 |
| JP | 2001527320 | 12/2001 |
| JP | 2002041578 | 2/2002 |
| JP | 2002044689 | 2/2002 |
| JP | 2002505019 | 2/2002 |
| JP | 2002092504 | 3/2002 |
| JP | 2002117217 | 4/2002 |
| JP | 2002133283 | 5/2002 |
| JP | 2002135757 | 5/2002 |
| JP | 2002515684 | 5/2002 |
| JP | 2002185416 | 6/2002 |
| JP | 3546021 | 8/2002 |
| JP | 2002236776 | 8/2002 |
| JP | 2002245192 | 8/2002 |
| JP | 2002304185 | 10/2002 |
| JP | 2002318874 | 10/2002 |
| JP | 2002532952 | 10/2002 |
| JP | 2002354507 | 12/2002 |
| JP | 2003500980 | 1/2003 |
| JP | 2003058688 | 2/2003 |
| JP | 2003219286 | 7/2003 |
| JP | 2003530763 | 10/2003 |
| JP | 2003331106 | 11/2003 |
| JP | 2004013472 | 1/2004 |
| JP | 2004021778 | 1/2004 |
| JP | 2004040822 | 2/2004 |
| JP | 3512419 | 3/2004 |
| JP | 2004102651 | 4/2004 |
| JP | 2004147036 | 5/2004 |
| JP | 2004206529 | 7/2004 |
| JP | 2004536477 | 12/2004 |
| JP | 2004536501 | 12/2004 |
| JP | 2005085207 | 3/2005 |
| JP | 2005130351 | 5/2005 |
| JP | 2005515669 | 5/2005 |
| JP | 2005525002 | 8/2005 |
| JP | 2005311739 | 11/2005 |
| JP | 2005352807 | 12/2005 |
| JP | 2006505145 | 2/2006 |
| JP | 2006139354 | 6/2006 |
| JP | 2006237817 | 9/2006 |
| JP | 2007088808 | 4/2007 |
| JP | 2007297146 | 11/2007 |
| JP | 2008009442 | 1/2008 |
| JP | 2008508529 | 3/2008 |
| JP | 2008508618 | 3/2008 |
| JP | 2008085767 | 4/2008 |
| JP | 2008276298 | 11/2008 |
| JP | 2009003736 | 1/2009 |
| JP | 2009507301 | 2/2009 |
| KR | 930006664 | 7/1993 |
| KR | 930006665 | 7/1993 |
| KR | 0168860 | 3/1999 |
| KR | 20010039360 | 5/2001 |
| KR | 1020020021695 | 3/2002 |
| KR | 20030063640 | 7/2003 |
| KR | 1020040104195 | 12/2004 |
| KR | 20050026920 | 3/2005 |
| KR | 20050044398 | 5/2005 |
| KR | 20050058296 | 6/2005 |
| KR | 20050083808 | 8/2005 |
| KR | 20050106393 | 11/2005 |
| KR | 20060055347 | 5/2006 |
| KR | 20070039123 | 4/2007 |
| KR | 20070051879 | 5/2007 |
| KR | 20070083528 | 8/2007 |
| KR | 20070083530 | 8/2007 |
| KR | 20070112412 | 11/2007 |
| KR | 20080034048 | 4/2008 |
| KR | 20080045258 | 5/2008 |
| KR | 20080059587 | 6/2008 |
| KR | 20080064176 | 7/2008 |
| KR | 20090003450 | 1/2009 |
| WO | 9111062 | 7/1991 |
| WO | 9307689 | 4/1993 |
| WO | 9526106 | 9/1995 |
| WO | 9745973 | 12/1997 |
| WO | 9832251 | 7/1998 |
| WO | 9927668 | 7/1999 |
| WO | 0004662 | 1/2000 |
| WO | 0035131 | 6/2000 |
| WO | 0067471 | 11/2000 |
| WO | 0072484 | 11/2000 |
| WO | 0108440 | 2/2001 |
| WO | 0219070 | 3/2002 |
| WO | 03044755 | 5/2003 |
| WO | 03053123 | 7/2003 |
| WO | 03060630 | 7/2003 |
| WO | 03071810 | 8/2003 |
| WO | 2004006110 | 1/2004 |
| WO | 2005038625 | 4/2005 |
| WO | 2006015188 | 2/2006 |

OTHER PUBLICATIONS

Akyildiz et al., "A Survey of Mobility Management in Next-Generation All-IP-Based Wireless Systems," IEEE Wireless Communications, Aug. 2004, 13 pages.

Berger et al., "Location Based Services in the Tourist Industry," Information Technology & Tourism, vol. 5, No. 4, Dec. 1, 2002, 19 pages.

Fitzgerald, "Evaluating Return on Investment of Multi-Media Advertising: A Retail Case Study," Presented at the 50 sup.th Annual ARF Convention and Trade Show, Apr. 28, 2004, 17 pages.

Rashid et al., "Implementing in Indoor/Urban Environments," Location Proceedings Based Information/Advertising for Existing Mobile Phone Users of the International Conference on Mobile Business (ICMB'05), 2005, downloaded Jan. 7, 2009, 7 pages.

Yu et al., "Matching User's Semantics With Data Semantics in Location-Based Services," Semantics in Mobile Environments (SME'05), May 9, 2005, 6 pages.

Fishkin et al, "Pervasive Computing," 4th International Conference, Pervasive 2006, Dublin, Ireland May 7-10, 2006, 415 pages.

Vildjiounaite et al., "Unobtrusive Multimodal Biometrics for Ensuring Privacy and Information Security with Personal Devices," Pervasive Computing, May 2006, 15 pages.

Mantyjarvi et al., "Identifying Users of Portable Devices from Gait Pattern with Accelerometers," IEEE International Conference on Acoustics, Speech, and Signal Processing (ICASSP'05), Mar. 18-23, 2005, 4 pages.

European Patent Office, "Extended European Search Report," issued in connection with European Patent Application No. 07812862.6, dated Jul. 6, 2009, 5 pages.

European Patent Office, "Extended European Search Report," issued in connection with European Patent Application No. 07812860.0 dated Jul. 6, 2009, 5 pages.

IP Australia, "Patent Examination Report No. 1," issued in connection with Australian Patent Application No. 2007272444, dated Dec. 24, 2012, 4 pages.

European Patent Office, "Extended European Search Report," issued in connection with European Patent Application No. 07840400.1, dated Jul. 6, 2009, 5 pages.

European Patent Office, "Extended European Search Report," issued in connection with European Patent Application No. 07812865.9, dated Jul. 16, 2009, 6 pages.

German Patent and Trademark Office, "German Official Action dated Oct. 14, 2002, Re Application 100 84 633.5-53," issued in connection with German Patent Application No. 10084633.5-53, dated Oct. 14, 2002, 5 pages.

International Preliminary Examining Authority, "International Preliminary Examination Report," issued in connection with International Patent Application No. PCT/US94/07746, dated Feb. 9, 1996, 4 pages.

(56) References Cited

OTHER PUBLICATIONS

International Preliminary Examining Authority, "Written Opinion," issued in connection with International Patent Application No. PCT/US94/07746, dated Aug. 17, 1995, 4 pages.
International Searching Authority, "International Search Report," issued in connection with International Patent Application No. PCT/US94/07746, dated Nov. 30, 1994, 4 pages.
Canadian Intellectual Property Office, "Office Action," issued in connection with Canadian Patent Application No. 2,168,540, dated Jan. 20, 2004, 2 pages.
Korean Intellectual Property Office, "Office Action," issued in connection with Korean Patent Application 10-2009-7002931, dated Apr. 23, 2014, 9 pages.
Korean Intellectual Property Office, "Office Action," issued in connection with Korean Patent Application No. 10-2009-7002929, dated May 14, 2014, 5 pages.
Ip Australia, "Patent Examination Report No. 1," issued in connection with Australian Patent Application No. 2007272440, dated Aug. 1, 2012, 3 pages.
State Intellectual Property Office of the People's Republic of China, "Rejection Decision," issued in connection with Chinese Patent Application No. 200780033751.1, dated Mar. 1, 2012, 10 pages.
Israel Patent Office, "Office Action," issued in connection with Israeli Patent Application No. 196435, dated Mar. 2, 2014, 3 pages.
Mexico Patent Office, "Office Action," issued in connection with Mexican Patent Application No. MX/a/2009/000468, dated Dec. 26, 2013, 4 pages.
United States Patent and Trademark Office, "Examiner's Answer to Appeal Brief," issued in connection with U.S. Appl. No. 11/776,940 dated Nov. 14, 2011, 13 pages.
United States Patent and Trademark Office, "Advisory Action," issued in connection with U.S. Appl. No. 11/776,940, dated Oct. 7, 2010, 3 pages.
United States Patent and Trademark Office, "Final Office Action," issued in connection with U.S. Appl. No. 11/776,940 dated Jul. 20, 2010, 10 pages.
United States Patent and Trademark Office, "Non-Final Office Action," issued in connection with U.S. Appl. No. 11/776,940 dated Oct. 9, 2009, 9 pages.
United States Patent and Trademark Office, "Advisory Action," issued in connection with U.S. Appl. No. 11/776,940 dated Jul. 9, 2009, 6 pages.
United States Patent and Trademark Office, "Final Office Action," issued in connection with U.S. Appl. No. 11/776,940 dated Apr. 21, 2009, 8 pages.
United States Patent and Trademark Office, "Non-Final Office Action," issued in connection with U.S. Appl. No. 11/776,940 dated Aug. 6, 2008, 7 pages.
International Searching Authority, "International Search Report and Written Opinion," issued in connection with International Patent Application No. PCT/US07/73376, dated Sep. 9, 2008, 9 pages.
United States Patent and Trademark Office, "Pre-Appeal Conference Decision," issued in connection with U.S. Appl. No. 11/776,987, dated Jun. 10, 2015, 2 pages.
United States Patent and Trademark Office, "Restriction Requirement," issued in connection with U.S. Appl. No. 11/776,987 dated Aug. 5, 2008, 7 pages.
United States Patent and Trademark Office, "Non-Final Office Action," issued in connection with U.S. Appl. No. 11/776,987 dated Nov. 28, 2008, 11 pages.
United States Patent and Trademark Office, "Final Office Action," issued in connection with U.S. Appl. No. 11/776,987 dated Apr. 15, 2009, 13 pages.
United States Patent and Trademark Office, "Non-Final Office Action," issued in connection with U.S. Appl. No. 11/776,987 dated Aug. 10, 2009, 9 pages.
United States Patent and Trademark Office, "Final Office Action," issued in connection with U.S. Appl. No. 11/776,987 dated Feb. 22, 2010, 11 pages.
United States Patent and Trademark Office, "Non-Final Office Action," issued in connection with U.S. Appl. No. 11/776,987 dated Aug. 12, 2010, 11 pages.
United States Patent and Trademark Office, "Final Office Action," issued in connection with U.S. Appl. No. 11/776,987 dated Dec. 22, 2010, 14 pages.
United States Patent and Trademark Office, "Non-Final Office Action," issued in connection with U.S. Appl. No. 11/776,987 dated Apr. 14, 2011, 13 pages.
United States Patent and Trademark Office, "Final Office Action," issued in connection with U.S. Appl. No. 11/776,987 dated Oct. 6, 2011, 14 pages.
United States Patent and Trademark Office, "Advisory Action," issued in connection with U.S. Appl. No. 11/776,987 dated Jan. 12, 2012, 3 pages.
United States Patent and Trademark Office, "Non-Final Office Action," issued in connection with U.S. Appl. No. 11/776,987 dated Dec. 31, 2013, 13 pages.
United States Patent and Trademark Office, "Advisory Action," issued in connection with U.S. Appl. No. 11/776,987, dated Apr. 20, 2015, 3 pages.
International Searching Authority, "International Search Report and Written Opinion," issued in connection with International Patent Application No. PCT/US07/73383, dated Aug. 25, 2008, 9 pages.
IP Australia, "Patent Examination Report No. 1," issued in connection with Australian Patent Application No. 2007272428, dated Aug. 1, 2012, 3 pages.
State Intellectual Property Office of the People's Republic of China, "First Office Action," issued in connection with Chinese Patent Application No. 200780033681.X, dated Jun. 24, 2011, 14 pages.
State Intellectual Property Office of the People's Republic of China, "First Office Action," issued in connection with Chinese Patent Application No. 201210166556.9, dated Oct. 28, 2013, 14 pages.
Israel Patent Office, "Office Action," issued in connection with Application No. 196433, dated Mar. 17, 2014, 2 pages.
Mexico Patent Office, "Office Action," issued in connection with Mexican Patent Application No. MX/a/2009/000469, dated Jan. 3, 2014, 3 pages.
International Bureau, "International Preliminary Report on Patentability," issued in connection with International Patent Application No. PCT/US2007/073390, dated Jan. 13, 2009, 10 pages.
International Searching Authority, "International Search Report," issued in connection with International Patent Application No. PCT/US07/73390, dated Aug. 25, 2008, 1 page.
International Searching Authority, "Written Opinion," issued in connection with International Patent Application No. PCT/US07/73390, dated Aug. 25, 2008, 9 pages.
United States Patent and Trademark Office, "Non-Final Office Action," issued in connection with U.S. Appl. No. 11/777,012 dated Apr. 23, 2014, 9 pages.
United States Patent and Trademark Office, "Final Office Action" issued in connection with U.S. Appl. No. 11/777,012 dated Jul. 15, 2013, 15 pages.
United States Patent and Trademark Office, "Non-Final Office Action" issued in connection with U.S. Appl. No. 11/777,012 dated Feb. 1, 2013, 14 pages.
United States Patent and Trademark Office, "Final Office Action" issued in connection with U.S. Appl. No. 11/777,012 dated Jun. 23, 2011, 14 pages.
United States Patent and Trademark Office, "Non-Final Office Action" issued in connection with U.S. Appl. No. 11/777,012 dated Dec. 27, 2010, 12 pages.
United States Patent and Trademark Office, "Final Office Action" issued in connection with U.S. Appl. No. 11/777,012 dated Feb. 1, 2010, 13 pages.
United States Patent and Trademark Office, "Non-Final Office Action" issued in connection with U.S. Appl. No. 11/777,012 dated Jul. 8, 2009, 12 pages.
Ip Australia, "Patent Examination Report No. 1," issued in connection with Australian Patent Application No. 2007272442, dated Aug. 1, 2012, 3 pages.
Israel Patent Office, "Office Action," issued in connection with Israeli Patent Application No. 196434, dated Mar. 31, 2014, 3 pages.

(56) References Cited

OTHER PUBLICATIONS

Japan Patent Office, "Notice of Reasons for Rejection," issued in connection with Japanese Patent Application No. 2009-519700, dated Apr. 16, 2013, 5 pages.
Japan Patent Office, "Notice of Reasons for Rejection," issued in connection with Japanese Patent Application No. 2009-519700, dated Nov. 5, 2013, 4 pages.
Korean Intellectual Property Office, "Office Action," issued in connection with Korean Patent Application No. 10-2009-7002934, dated Oct. 16, 2013, 2 pages.
Mexico Patent Office, "Office Action," issued in connection with Mexican Patent Application No. MX/a/2009/000467, dated Jan. 3, 2014, 5 pages.
International Searching Authority, "International Search Report," issued in connection with International Patent Application No. PCT/US07/73393, dated Feb. 4, 2008, 3 pages.
United States Patent and Trademark Office, "Final Office Action," issued in connection with U.S. Appl. No. 11/777,030 dated Dec. 26, 2013, 20 pages.
United States Patent and Trademark Office, "Final Office Action," issued in connection with U.S. Appl. No. 11/777,030 dated Feb. 28, 2011, 26 pages.
United States Patent and Trademark Office, "Non-Final Office Action," issued in connection with U.S. Appl. No. 11/777,030 dated Sep. 20, 2010, 10 pages.
International Searching Authority, "International Search Report and Written Opinion," issued in connection with International Patent Application No. PCT/US07/73395, dated Aug. 8, 2008, 13 pages.
United States Patent and Trademark Office, "Examiner's Answer to Appeal Brief," issued in connection with U.S. Appl. No. 11/777,051 dated Aug. 2, 2012, 15 pages.
United States Patent and Trademark Office, "Advisory Action," issued in connection with U.S. Appl. No. 11/777,051 dated Sep. 26, 2011, 3 pages.
United States Patent and Trademark Office, "Final Office Action," issued in connection with U.S. Appl. No. 11/777,051 dated Jul. 1, 2011, 11 pages.
United States Patent and Trademark Office, "Non-Final Office Action," issued in connection with U.S. Appl. No. 11/777,051 dated Nov. 15, 2010, 8 pages.
United States Patent and Trademark Office, "Advisory Action," issued in connection with U.S. Appl. No. 11/777,051 dated Jul. 15, 2010, 3 pages.
United States Patent and Trademark Office, "Final Office Action," issued in connection with U.S. Appl. No. 11/777,051 dated Apr. 30, 2010, 9 pages.
United States Patent and Trademark Office, "Non-Final Office Action," issued in connection with U.S. Appl. No. 11/777,051 dated Jul. 14, 2009, 11 pages.
United States Patent and Trademark Office, "Requirement for Restriction/Election," issued in connection with U.S. Appl. No. 11/777,051 dated Mar. 23, 2009, 10 pages.
United States Patent and Trademark Office, "Notice of Allowance," issued in connection with U.S. Appl. No. 11/777,051, dated Jul. 5, 2016, 8 pages.
United States Patent and Trademark Office, "Decision on Appeal," issued in connection with U.S. Appl. No. 11/777,051, dated Aug. 26, 2015, 8 pages.
Government of India Patent Office, "First Examination Report," issued in connection with Indian Patent Application No. 574/KOLNP/2009, dated May 29, 2014, 2 pages.
International Searching Authority, "International Search Report and Written Opinion," issued in connection with International Patent Application No. PCT/US12/72276, dated Mar. 13, 2013, 12 pages.
Pellegrini, "Listen Without Prejudice,"Vue, Jun. 2005, retrieved from <http://wargod.arbitron.com/downloads/Vue PelligriniJune05.pdf>, retrieved on Feb. 7, 2013, 6 pages.

Hossain et al., "A Comprehensive Study of Bluetooth Signal Parameters for Localization," The 18th Annual IEEE International Symposium on Personal, Indoor and Mobile Radio Communications, Sep. 2007, 5 pages.
Azizyan et al., "SurroundSense: Mobile Phone Localization via Ambience Fingerprinting," MobiCom'09, Sep. 2009, 12 pages.
Bellettini et al., "A Framework for Robust Audio Fingerprinting," Journal of Communications, vol. 5, No. 5, May 2010, 16 pages.
Lau et al., "Enhanced RSSI-Based High Accuracy Real-Time User Location Tracking System for Indoor and Outdoor Environments," International Journal on Smart Sensing and Intelligent Systems, vol. 1, No. 2, Jun. 2008, 15 pages.
Pei et al., "Using Inquiry-Based Bluetooth RSSI Probability Distributions for Indoor Positioning," Journal of Global Positioning Systems, vol. 9, No. 2, 2010, 9 pages.
Government of India Patent Office, "First Examination Report," issued in connection with Indian Patent Application No. 577/KOLNP/2009, dated May 29, 2014, 2 pages.
Government of India Patent Office, "First Examination Report," issued in connection with Indian Patent Application No. 575/KOLNP/2009, dated May 29, 2014, 2 pages.
Government of India Patent Office, "First Examination Report," issued in connection with Indian Patent Application No. 573/KOLNP/2009, dated May 29, 2014, 2 pages.
Government of India Patent Office, "First Examination Report," issued in connection with Indian Patent Application No. 576/KOLNP/2009, dated Jun. 10, 2014, 2 pages.
International Bureau, "International Preliminary Report on Patentability," issued in connection with International Patent Application No. PCT/US2012/072276, dated Jul. 10, 2014, 6 pages.
United States Patent and Trademark Office, "Final Office Action," issued in connection with U.S. Appl. No. 13/341,113 dated Jun. 24, 2014, 14 pages.
United States Patent and Trademark Office, "Non-Final Office Action," issued in connection with U.S. Appl. No. 13/341,113 dated Jan. 31, 2014, 10 pages.
State Intellectual Property Office of People's Republic of China, "Second Office Action," issued in connection with Chinese Patent Application No. 201212166556.9 dated Jul. 11, 2014, 13 pages.
IP Australia, "Patent Examination Report No. 1," issued in connection with Australian Patent Application No. 2007272434, dated Aug. 6, 2012, 4 pages.
IP Australia, "Notice of Acceptance," issued in connection with Australian Patent Application No. 2007272434, dated May 8, 2014, 2 pages.
Canadian Intellectual Property Office, "Office Action," issued in connection with Canadian Patent Application No. 2,658,979, dated Jul. 31, 2014, 2 pages.
Canadian Intellectual Property Office, "Office Action," issued in connection with Canadian Patent Application No. 2,659,244, dated Aug. 22, 2014, 3 pages.
Canadian Intellectual Property Office, "Office Action," issued in connection with Canadian Patent Application No. 2,659,277, dated Aug. 22, 2014, 3 pages.
United States Patent and Trademark Office, "Non-Final Office Action," issued in connection with U.S. Appl. No. 13/341,453, dated Sep. 25, 2014, 9 pages.
United States Patent and Trademark Office, "Final Office Action," issued in connection with U.S. Appl. No. 11/777,012, dated Oct. 1, 2014, 11 pages.
United States Patent and Trademark Office, "Non-Final Office Action," issued in connection with U.S. Appl. No. 13/341,113, dated Oct. 10, 2014, 17 pages.
United States Patent and Trademark Office, "Final Office Action," issued in connection with U.S. Appl. No. 11/776,987, dated Dec. 24, 2014, 20 pages.
Helgeson et al., "Determinants of Mail-Survey Response: Survey Design Factors and Respondent Factors," vol. 19, No. 3, Mar. 2002, 26 pages.
Groves et al., "Understanding the Decision to Participate in a Survey," Public Opinion Quarterly, vol. 56, No. 4, Jan. 1, 1992, 21 pages.

(56) References Cited

OTHER PUBLICATIONS

United States Patent and Trademark Office, "Decision on Appeal," issued in connection with U.S. Appl. No. 11/776,940, dated Dec. 12, 2014, 11 pages.
United States Patent and Trademark Office, "Advisory Action," issued in connection with U.S. Appl. No. 11/777,012, dated Mar. 4, 2015, 4 pages.
Mexican Industrial Property Institute, "Notice of Allowance," issued in connection with Mexican Patent Application No. MX/a/2009/000469, dated Mar. 5, 2015, 2 pages.
State Intellectual Property Office of the People's Republic of China, "Second Office Action," issued in connection with Chinese Patent Application No. 200780033751.1, dated Mar. 25, 2015, 27 pages.
United States Patent and Trademark Office, "Non-Final Office Action," issued in connection with U.S. Appl. No. 13/728,252, dated Apr. 16, 2015, 12 pages.
State Intellectual Property Office of the People's Republic of China, "Third Office Action," issued in connection with Chinese Patent Application No. 201210166556.9, dated Apr. 8, 2015, 9 pages.
United States Patent and Trademark Office, "Final Office Action," issued in connection with U.S. Appl. No. 13/341,113, dated May 13, 2015, 20 pages.
IP Australia, "Patent Examination Report No. 1," issued in connection with Australian Patent Application No. 2014202095, dated May 25, 2015, 3 pages.
Korean Intellectual Property Office, "Final Rejection," issued in connection with Korean Patent Application No. 10-2009-7002929, dated May 22, 2015, 5 pages.
Canadian Intellectual Property Office, "Office Action," issued in connection with Canadian Patent Application No. 2,659,244, dated May 20, 2015, 5 pages.
Israel Patent Office, "Office Action," issued in connection with Israeli Patent Application No. 196433, dated May 31, 2015, 4 pages.
Canadian Intellectual Property Office, "Office Action," issued in connection with Canadian Patent Application No. 2,659,277, dated Jul. 9, 2015, 5 pages.
United States Patent and Trademark Office, "Final Office Action," issued in connection with U.S. Appl. No. 13/728,252, dated Aug. 11, 2015, 17 pages.
United States Patent and Trademark Office, "Advisory Action," issued in connection with U.S. Appl. No. 13/341,113, dated Aug. 27, 2015, 3 pages.
United States Patent and Trademark Office, "Notice of Allowance," issued in connection with U.S. Appl. No. 13/728,252, dated Oct. 23, 2015, 6 pages.
State Intellectual Property Office of the People's Republic of China, "Office Action," issued in connection with Chinese Patent Application No. 201310263540.4, dated Nov. 3, 2015, 11 pages.
State Intellectual Property Office of the People's Republic of China, "Office Action," issued in connection with Chinese Patent Application No. 201310556658.6, dated Jan. 12, 2016, 6 pages.
United States Patent and Trademark Office, "Non-Final Office Action," issued in connection with U.S. Appl. No. 11/777,012, dated Feb. 11, 2016, 16 pages.
European Patent Office, "Summons to attend oral proceedings pursuant to Rule 115(a) EPC," issued in connection with European Patent Application No. 07840400.1, dated Mar. 14, 2016, 7 pages.
United States Patent and Trademark Office, "Corrected Notice of Allowability," issued in connection with U.S. Appl. No. 13/728,252, dated Mar. 18, 2016, 2 pages.
United States Patent and Trademark Office, "Pre-Appeal Conference Decision," issued in connection with U.S. Appl. No. 11/777,012, dated May 18, 2015, 2 pages.
United States Patent and Trademark Office, "Notice of Allowance," issued in connection with U.S. Appl. No. 11/777,051, dated Apr. 11, 2016, 7 pages.
United States Patent and Trademark Office, "Pre-Brief Appeal Conference Decision," issued in connection with U.S. Appl. No. 11/777,051, dated Nov. 22, 2010, 2 pages.
United States Patent and Trademark Office, "Pre-Brief Appeal Conference Decision," issued in connection with U.S. Appl. No. 11/777,051, dated Feb. 9, 2012, 2 pages.
United States Patent and Trademark Office, "Non-Final Office Action," issued in connection with U.S. Appl. No. 15/331,510, dated Apr. 10, 2018, 14 pages.
United States Patent and Trademark Office, "Final Office Action," issued in connection with U.S. Appl. No. 15/331,510, dated Dec. 6, 2018, 20 pages.
United States Patent and Trademark Office, "Advisory Action," issued in connection with U.S. Appl. No. 15/331,510, dated Feb. 21, 2019, 3 pages.
United States Patent and Trademark Office, "Notice of Allowance," issued in connection with U.S. Appl. No. 15/331,510, dated Apr. 5, 2019, 12 pages.

* cited by examiner

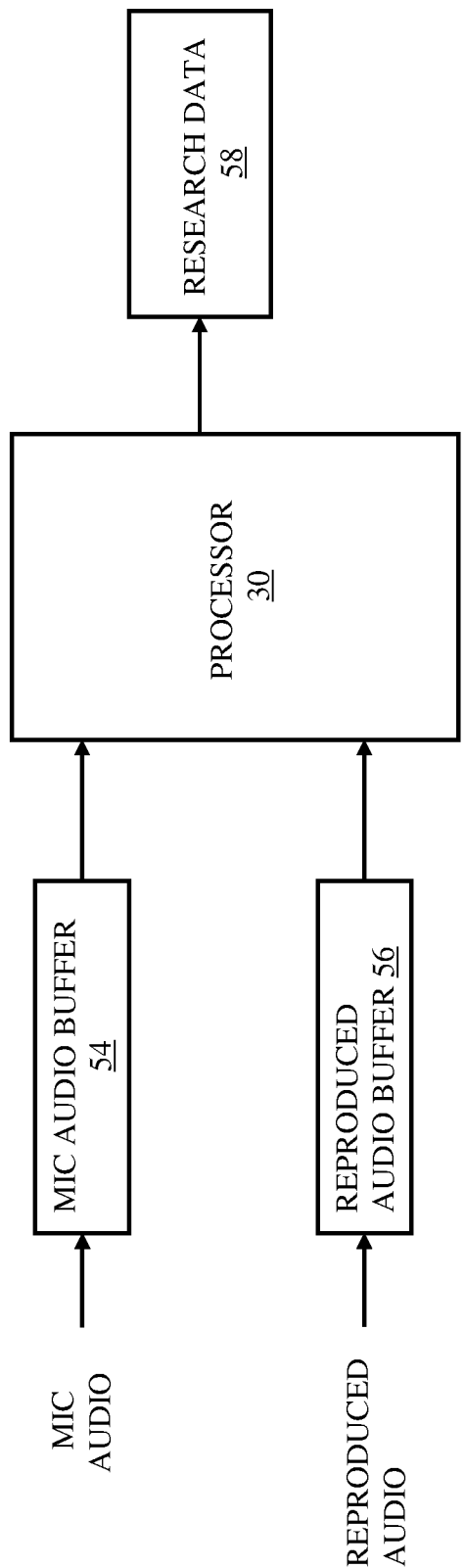

METHODS AND SYSTEMS FOR COMPLIANCE CONFIRMATION AND INCENTIVES

Methods and systems for monitoring use of research devices by users are disclosed. Systems and methods are disclosed that are useful for monitoring use of research devices in accordance with predetermined criteria, providing incentives for compliant use thereof and/or analyzing data relating to the use thereof.

BACKGROUND

Research operations are conducted by establishing a panel of participants, often referred to as panelists. In some research operations, the panelists are provided with portable monitoring devices to gather research data. In other research operations the panelists' own portable devices are employed to gather research data. In either case, the panelists are instructed to carry the portable devices with them during the day for gathering research data, such as data indicating exposure to media and/or other market research data.

Those who pay to use such market research data want to be assured that the data is reliable. In particular, if the portable monitor was not actually carried about by a panelist during the day, whatever data has been collected by the portable monitor does not reflect the experience of a panelist. Accordingly, those who pay for use of such research data want reasonable assurances from the research organization that the portable monitors used to gather the data have actually been carried about by individuals or at least accompany individuals during the times that research data is collected by such monitors.

Arbitron Inc., which pioneered the use of portable monitors for gathering research data, has developed and implemented techniques to provide such assurances to those who license its research data. Such techniques are the subject of U.S. Pat. No. 5,483,276 issued Jan. 9, 1996 in the names of Brooks, et al., which is owned by the assignee of the present application and is hereby incorporated herein by reference in its entirety.

DISCLOSURE

For this application, the following terms and definitions shall apply:

The term "data" as used herein means any indicia, signals, marks, symbols, domains, symbol sets, representations, and any other physical form or forms representing information, whether permanent or temporary, whether visible, audible, acoustic, electric, magnetic, electromagnetic or otherwise manifested. The term "data" as used to represent predetermined information in one physical form shall be deemed to encompass any and all representations of corresponding information in a different physical form or forms.

The terms "media data" and "media" as used herein mean data which is widely accessible, whether over-the-air, or via cable, satellite, network, internetwork (including the Internet), print, displayed, distributed on storage media, or by any other means or technique that is humanly perceptible, without regard to the form or content of such data, and including but not limited to audio, video, audio/video, text, images, animations, databases, broadcasts, displays (including but not limited to video displays, posters and billboards), signs, signals, web pages, print media and streaming media data.

The term "research data" as used herein means data comprising (1) data concerning usage of media, (2) data concerning exposure to media, and/or (3) market research data.

The term "presentation data" as used herein shall mean media data, content other than media data or a message to be presented to a user.

The term "database" as used herein means an organized body of related data, regardless of the manner in which the data or the organized body thereof is represented. For example, the organized body of related data may be in the form of a table, a map, a grid, a packet, a datagram, a frame, a file, an e-mail, a message, a document, a list or in any other form.

The term "correlate" as used herein means a process of ascertaining a relationship between or among data, including but not limited to an identity relationship, a correspondence or other relationship of such data to further data, inclusion in a dataset, exclusion from a dataset, a predefined mathematical relationship between or among the data and/or to further data, and the existence of a common aspect between or among the data.

The terms "purchase" and "purchasing" as used herein mean a process of obtaining title, a license, possession or other right in or to goods or services in exchange for consideration, whether payment of money, barter or other legally sufficient consideration, or as promotional samples. As used herein, the term "goods" and "services" include, but are not limited to, data and rights in or to data.

The term "network" as used herein includes both networks and internetworks of all kinds, including the Internet, and is not limited to any particular network or inter-network.

The terms "first," "second," "primary," and "secondary" are used herein to distinguish one element, set, data, object, step, process, function, activity or thing from another, and are not used to designate relative position, arrangement in time or relative importance, unless otherwise stated explicitly.

The terms "coupled", "coupled to", and "coupled with" as used herein each mean a relationship between or among two or more devices, apparatus, files, circuits, elements, functions, operations, processes, programs, media, components, networks, systems, subsystems, and/or means, constituting any one or more of (a) a connection, whether direct or through one or more other devices, apparatus, files, circuits, elements, functions, operations, processes, programs, media, components, networks, systems, subsystems, or means, (b) a communications relationship, whether direct or through one or more other devices, apparatus, files, circuits, elements, functions, operations, processes, programs, media, components, networks, systems, subsystems, or means, and/or (c) a functional relationship in which the operation of any one or more devices, apparatus, files, circuits, elements, functions, operations, processes, programs, media, components, networks, systems, subsystems, or means depends, in whole or in part, on the operation of any one or more others thereof.

The terms "communicate" and "communicating" as used herein include both conveying data from a source to a destination, and delivering data to a communications medium, system, channel, network, device, wire, cable, fiber, circuit, and/or link to be conveyed to a destination. The term "communications" as used herein includes one or more of a communications medium, system, channel, network, device, wire, cable, fiber, circuit and link.

The term "message" as used herein includes data to be communicated, in communication or which has been communicated.

The term "processor" as used herein means processing devices, apparatus, programs, circuits, components, systems and subsystems, whether implemented in hardware, software or both, and whether or not programmable. The term "processor" as used herein includes, but is not limited to one or more computers, hardwired circuits, signal modifying devices and systems, devices and machines for controlling systems, central processing units, programmable devices and systems, field programmable gate arrays, application specific integrated circuits, systems on a chip, systems comprised of discrete elements and/or circuits, state machines, virtual machines, data processors, processing facilities and combinations of any of the foregoing.

The terms "storage" and "data storage" as used herein mean data storage devices, apparatus, programs, circuits, components, systems, subsystems and storage media serving to retain data, whether on a temporary or permanent basis, and to provide such retained data.

The terms "panelist," "panel member" and "participant" are interchangeably used herein to refer to a person who is, knowingly or unknowingly, participating in a study to gather information, whether by electronic, survey or other means, about that person's activity.

The term "household" as used herein is to be broadly construed to include family members, a family living at the same residence, a group of persons related or unrelated to one another living at the same residence, and a group of persons (of which the total number of unrelated persons does not exceed a predetermined number) living within a common facility, such as a fraternity house, an apartment or other similar structure or arrangement.

The term "activity" as used herein includes, but is not limited to, purchasing conduct, shopping habits, viewing habits, computer, Internet usage, exposure to media, personal attitudes, awareness, opinions and beliefs, as well as other forms of activity discussed herein.

The term "portable user appliance" (also referred to herein, for convenience, by the abbreviation "PUA") as used herein means an electrical or non-electrical device capable of being carried by or on the person of a user or capable of being disposed on or in, or held by, a physical object (e.g., attaché, purse) capable of being carried by or on the user, and having at least one function of primary benefit to such user, including without limitation, a cellular telephone, a personal digital assistant ("FDA"), a Blackberry® device, a radio, a television, a game system (e.g., a Gameboy® device), a notebook computer, a laptop computer, a GPS device, a personal audio device (e.g., an MP3 player), a DVD player, a two-way radio, a personal communications device, a telematics device, a remote control device, a wireless headset, a wristwatch, a portable data storage device (e.g., Thumb™ drive), a camera, a recorder, a keyless entry device, a ring, a comb, a pen, a pencil, a notebook, a wallet, a tool, a flashlight, an implement, a pair of glasses, an article of clothing, a belt, a belt buckle, a fob, an article of jewelry, an ornamental article, a pair of shoes or other foot garment (e.g., sandals), a jacket, and a hat, as well as any devices combining any of the foregoing or their functions.

The term "research device" as used herein shall mean (1) a portable user appliance configured or otherwise enabled to gather, store and/or communicate research data, or to cooperate with other devices to gather, store and/or communicate research data, and/or (2) a research data gathering, storing and/or communicating device.

The term "user-beneficial function" as used herein shall mean a function initiated or carried out by a person with the use of a PUA, which function is of primary benefit to that person.

A method of monitoring use by a user of a portable research device, comprising: producing monitored data by monitoring at least one of the user's heart activity, the user's breathing activity, the user's borborygmus (gastrointestinal noise), the user's gait, the user's data input to the portable research device, the user's keyboard usage characteristics, the user's vascular pattern, the user's facial and/or ear patterns, the user's signature, the user's fingerprint and/or handprint, the user's hand geometry, the user's retinal and/or iris pattern, the user's airborne biochemical indicators, the user's muscular activity, and an impact of the portable research device with another object; and determining whether use of the portable research device by the user is in accordance with at least one predetermined criterion based on the monitored data.

A system for monitoring use by a user of a portable research device comprises a monitor for producing monitored data by monitoring at least one of the user's heart activity, the user's breathing activity, the user's borborygmus, the user's gait, the user's data input to the portable research device, the user's keyboard usage characteristics, the user's vascular pattern, the user's facial and/or ear patterns, the user's signature, the user's fingerprint and/or handprint, the user's hand geometry, the user's retinal and/or iris pattern, the user's airborne biochemical indicators, the user's muscular activity, and an impact of the portable research device with another object; and a processor coupled with the monitor to receive the monitored data and operative to determine whether use of the portable research device by the user is in accordance with at least one predetermined criterion based on the monitored data.

A method of monitoring use by a user of a portable research device in accordance with at least one predetermined use criterion comprises producing passively monitored data in a portable research device, communicating a request message to the portable research device from a monitoring system, automatically producing a response message using the portable research device, the response message including and/or based on the passively monitored data, communicating the response message to the monitoring system and, determining in the monitoring system whether the use of the PUA complies with at least one predetermined use criterion based on the passively monitored data.

A method of monitoring use by a user of a portable research device in accordance with at least one predetermined use criterion comprises communicating a request message to the portable research device, the request message requesting data representing an ability of the portable research device to gather, store and/or communicate research data; receiving a response message communicated from the portable research device including the requested data; and storing data indicating whether the user is in compliance with the at least one predetermined use criterion and/or a level of the user's compliance therewith based on the received data.

A system for monitoring use by a user of a portable research device in accordance with at least one predetermined use criterion comprises communications operative to communicate a request message to the portable research device, the request message requesting data representing an ability of the portable research device to gather, store and/or communicate research data; the communications being operative to receive a response message communicated from the portable research device including the requested data; a processor coupled with the communications to produce data indicating whether the user is in compliance with the at least one predetermined use criterion and/or a level of the user's compliance therewith based on the received data; and storage coupled with the processor to receive and store the compliance data.

A method of monitoring use by a user of a portable research device in accordance with at least one predetermined use criterion comprises communicating a request message to the portable research device, the request message requesting data representing a power capacity of the portable research device; receiving a response message communicated from the portable research device including the requested data; and storing data indicating whether the user is in compliance with the at least one predetermined use criterion and/or a level of the user's compliance therewith based on the received data.

A system for monitoring use by a user of a portable research device in accordance with at least one predetermined use criterion comprises communications operative to communicate a request message to the portable research device, the request message requesting data representing a power capacity of the portable research device; the communications being operative to receive a response message communicated from the portable research device including the requested data; a processor coupled with the communications to produce data indicating whether the user is in compliance with the at least one predetermined use criterion and/or a level of the user's compliance therewith based on the received data; and storage coupled with the processor to receive and store the compliance data.

A method for monitoring use by a user of a portable research device in accordance with at least one predetermined use criterion comprises passively gathering data for assessing an identity of a user of the portable research device; processing the passively gathered data to produce assessment data indicating a possibility that the user is not a predetermined correct user of the portable research device; based on the assessment data, presenting a message to the user requesting a response from which the user's identity may be determined; and processing a response to the message to produce data indicating whether the user is the predetermined correct user.

Certain embodiments of the methods and systems are presented in the following disclosure in conjunction with the accompanying drawings, in which:

FIG. 8A is a functional block diagram for use in explaining certain embodiments involving the use of the cellular telephone of FIG. 8;

Figure 1A:
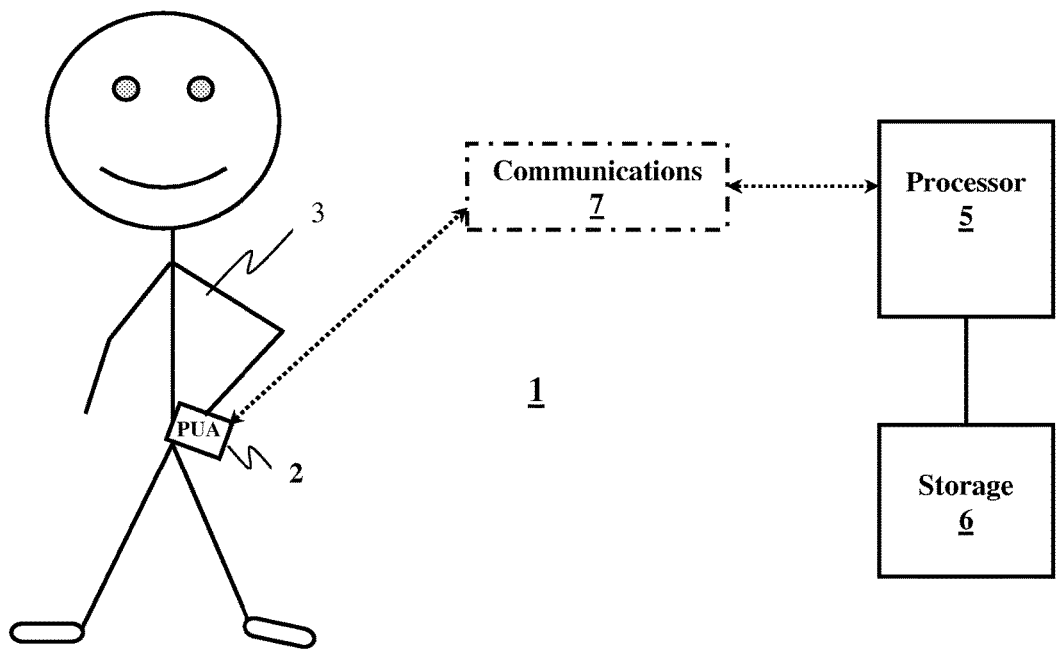
FIG. 1A illustrates various monitoring systems that include a portable user appliance ("PUA") used by a user and configured to operate as a research device.

A method of monitoring use by a user of a research device in accordance with at least one predetermined use criterion comprises communicating a request message to the research device, the request message requesting a response from the user of the research device; receiving a response message communicated from the research device in response to the request message; and storing data indicating whether the user is in compliance with the at least one predetermined use criterion and/or a level of the user's compliance therewith.

A system for monitoring use by a user of a research device in accordance with at least one predetermined use criterion comprises communications operative to communicate a request message to the research device, the request message requesting a response from the user of the research device; the communications being operative to receive a response message communicated from the research device in response to the request message; a processor coupled with the communications to receive the response message and operative to produce compliance data indicating whether the user is in compliance with the at least one predetermined use criterion and/or a level of the user's compliance therewith; and storage coupled with the processor to receive and store the compliance data.

A method of monitoring use by a user of a research device in accordance with at least one predetermined use criterion comprises communicating a request message to the research device, the request message requesting data of a predetermined type permitting an identification of the user of the research device; receiving a response message communicated from the research device including data of the predetermined type; evaluating an identity of the user based on the received data to produce identification data; and storing data indicating whether the user is in compliance with the at least one predetermined use criterion and/or a level of the user's compliance therewith based on the identification data.

A system for monitoring use by a user of a research device in accordance with at least one predetermined use criterion comprises communications operative to communicate a request message to the research device, the request message requesting data of a predetermined type permitting an identification of the user of the research device; the communications being operative to receive a response message communicated from the research device including data of the predetermined type; a processor coupled with the communications to evaluate an identity of the user based on the received data to produce identification data; and storage coupled with the processor to receive and store data indicating whether the user is in compliance with the at least one predetermined use criterion and/or a level of the user's compliance therewith based on the identification data.

A method of monitoring use by a user of a research device in accordance with at least one predetermined use criterion comprises communicating a request message to the research device, the request message requesting a response from the user of the research device; receiving a response message communicated from the research device in response to the request message; and producing compliance data indicating (a) whether use of the research device by the user is in compliance with the at least one predetermined use criterion and/or (b) a level of the user's compliance with the at least one predetermined use criterion.

A system for monitoring use by a user of a research device in accordance with at least one predetermined use criterion comprises communications operative to communicate a request message to the research device, the request message requesting a response from the user of the research device; the communications being operative to receive a response message communicated from the research device in response to the request message; and a processor coupled with the communications to receive the response message and to produce compliance data indicating (a) whether use of the research device by the user is in compliance with the at least one predetermined use criterion and/or (b) a level of the user's compliance with the at least one predetermined use criterion.

A method of monitoring use by a pre-selected user of a research device comprises producing monitored data by monitoring at least one of a biometric parameter of the user, the user's data input to the research device, a personal identification signal from a device in or on the person of the user, sounds external to the research device and a location or change in a location of the research device; producing identification data identifying the user based on the monitored data; and determining whether the research device is being used by the user in accordance with at least one predetermined criterion based on the identification data.

A system for monitoring use by a pre-selected user of a research device comprises a monitor operative to produce monitored data by monitoring at least one of a biometric parameter of the user, the user's data input to the research device, a personal identification signal from a device in or on the person of the user, sounds external to the research device and a location or change in a location of the research device; and a processor coupled with the monitor to receive the monitored data and operative to produce identification data identifying the user based on the monitored data and to produce compliance data indicating whether the research device is being used by the user in accordance with at least one predetermined criterion based on the identification data. In certain embodiments, the system comprises a device adapted to be carried in or on the person of the user and operative to emit the personal identification signal.

A method of monitoring use by a user of a research device in accordance with at least one predetermined use criterion comprises actively monitoring use of the research device by the user by communicating a message to the user requesting a response; and passively monitoring use of the research device by the user by sensing at least one parameter indicating whether the research device is being used in accordance with the at least one predetermined criterion.

A system for monitoring use by a user of a research device in accordance with at least one predetermined use criterion comprises a first monitoring subsystem operative to actively monitor use of the research device by the user by communicating a message to the user requesting a response; and a second monitoring subsystem operative to passively monitor use of the research device by the user by sensing at least one parameter indicating whether the research device is being used in accordance with the at least one predetermined criterion.

A method of promoting use of a research device by a user in compliance with at least one predetermined use criterion comprises producing compliance data for a plurality of different times indicating whether the research device is being used in compliance with the at least one predetermined use criterion; producing level data representing a level of compliance by the user based on the compliance data; and communicating a message to the user indicating a level of compliance of the user based on the level data.

A system for promoting use of a research device by a user in compliance with at least one predetermined use criterion comprises a processor operative to produce compliance data for a plurality of different times indicating whether the research device is being used in compliance with the at least one predetermined use criterion and to produce level data representing a level of compliance by the user based on the compliance data; and communications operative to communicate a message to the user indicating a level of compliance of the user based on the level data.

A method of promoting use of research devices by a plurality of research device users in compliance with at least one predetermined use criterion comprises producing level data representing relative compliance levels of each of a plurality of research device users; and communicating a message to each of the plurality of users indicating the user's compliance relative to others of the plurality of research device users.

A system for promoting use of research devices by a plurality of research device users in compliance with at least one predetermined use criterion comprises a processor operative to produce level data representing relative compliance levels of each of a plurality of research device users; and communications coupled with the processor to receive the level data and operative to communicate a message to each of the plurality of users indicating the user's compliance relative to others of the plurality of research device users based on the level data.

A method of gathering data concerning usage of a PUA comprises monitoring usage of the PUA to produce usage data within the PUA; and communicating the usage data from the PUA to a usage data processing facility.

A system for gathering data concerning usage of a PUA comprises a monitor in or on the PUA and operative to monitor usage of the PUA to produce usage data; and communications coupled with the monitor to receive the usage data and operative to communicate the usage data from the PUA to a usage data processing facility.

A method of monitoring use of a PUA by a user, the PUA including a communication interface for communicating with at least another PUA comprises detecting communication by the communication interface of the PUA; providing communication data relating to the communication of the PUA; and providing trend data representing at least one trend of usage of the PUA by the user based on the communication data.

A system for monitoring use of a PUA by a user, the PUA including a communication interface for communicating with at least another PUA comprises a monitor operative to detect communication by the communication interface of the PUA and to produce communication data relating to the communication of the PUA; and a processor coupled with the monitor to receive the communication data and operative to provide trend data representing at least one trend of usage of the PUA by the user based on the communication data.

A method of monitoring use by a user of a research device in accordance with at least one predetermined use criterion comprises producing monitored data by means of the research device representing at least two of the following parameters: the user's heart activity, pulse, breathing, borborygmus, gait, voice, keyboard usage characteristics, body temperature, vascular pattern, facial pattern, ear pattern, signature, fingerprint, palm print, handprint, hand geometry, retinal pattern, iris pattern, airborne biochemical indicators, muscular activity, or other biometric parameter, a presence indication signal or personal identification signal from a device in or on the person of the user, remaining power capacity of the research device, recharging of the research device, location of the research device, change in location of the research device, data input to the research device, sounds external to the research device, motion of the research device, pressure applied to the research device and an impact of the research device with another object; and producing compliance data based on the monitored data indicating whether the user has complied with the at least one predetermined use criterion.

A system for monitoring use by a user of a research device in accordance with at least one predetermined use criterion comprises a sensor/detector operative to produce monitored data by means of the research device representing at least two of the following parameters: the user's heart activity, pulse, breathing, borborygmus, gait, voice, keyboard usage characteristics, body temperature, vascular pattern, facial pattern, ear pattern, signature, fingerprint, palm print, handprint, hand geometry, retinal pattern, iris pattern, airborne biochemical indicators, muscular activity, or other biometric parameter, a presence indication signal or personal identification signal from a device in or on the person of the user, remaining power capacity of the research device, recharging of the research device, location of the research device, change in location of the research device, data input to the research device, sounds external to the research device, motion of the research device, pressure applied to the research device and an impact of the research device with another object; and a processor operative to produce compliance data based on the monitored data indicating whether the user has complied with the at least one predetermined use criterion. In certain embodiments, the system comprises a device adapted to be carried in or on the person of the user and operative to emit the presence indication signal or personal identification signal.

Numerous types of research operations carried out with the use of research devices are possible, including, without limitation, television and radio program audience measurement; exposure to advertising in various media, such as television, radio, print and outdoor advertising, among others; consumer spending habits; consumer shopping habits including the particular retail stores and other locations visited during shopping and recreational activities; travel patterns, such as the particular routes taken between home and work, and other locations; consumer attitudes, beliefs, awareness and preferences; and so on. For the desired type of media and/or market research operation to be conducted, particular activity of individuals is monitored. In research operations research data relating to two or more of the foregoing are gathered, while in others only one kind of such data is gathered.

Various monitoring techniques are suitable. For example, television viewing or radio listening habits, including exposure to commercials therein, are monitored utilizing a variety of techniques. In certain techniques, acoustic energy to which an individual is exposed is monitored to produce data which identifies or characterizes a program, song, station, channel, commercial, etc. that is being watched or listened to by the individual. Where audio media includes ancillary codes that provide such information, suitable decoding techniques are employed to detect the encoded information, such as those disclosed in U.S. Pat. Nos. 5,450,490 and 5,764,763 to Jensen, et al., U.S. Pat. No. 5,579,124 to Aijala, et al., U.S. Pat. Nos. 5,574,962, 5,581,800 and 5,787,334 to Fardeau, et al., U.S. Pat. No. 6,871,180 to Neuhauser, et al., U.S. Pat. No. 6,862,355 to Kolessar, et al. issued Mar. 1, 2005 and U.S. Pat. No. 6,845,360 to Jensen, et al., issued Jan. 18, 2005, each of which is assigned to the assignee of the present application and all of which are incorporated herein by reference in their entireties.

Still other suitable decoding techniques are the subject of PCT Publication WO 00/04662 to Srinivasan, U.S. Pat. No. 5,319,735 to Preuss, et al., U.S. Pat. No. 6,175,627 to Petrovich, et al., U.S. Pat. No. 5,828,325 to Wolosewicz, et al., U.S. Pat. No. 6,154,484 to Lee et al., U.S. Pat. No. 5,945,932 to Smith, et al., PCT Publication WO 99/59275 to Lu, et al., PCT Publication WO 98/26529 to Lu, et al., and PCT Publication WO 96/27264 to Lu, et al., U.S. Pat. No. 7,006,555 to Srinivasan, U.S. Pat. No. 6,968,564 to Srinivasan, PCT publication WO 05/99385 to Ramaswamy, et al., U.S. Pat. No. 6,879,652 to Srinivasan, U.S. Pat. No. 6,621, 881 to Srinivasan and U.S. Pat. No. 6,807,230 to Srinivasan all of which are incorporated herein by reference in their entireties In some cases a signature is extracted from transduced media data for identification by matching with reference signatures of known media data. Suitable techniques for this purpose include those disclosed in U.S. Pat. No. 5,612,729 to Ellis, et al. and in U.S. Pat. No. 4,739,398 to Thomas, et al., each of which is assigned to the assignee of the present application and both of which are incorporated herein by reference in their entireties.

Still other suitable techniques are the subject of U.S. Pat. No. 2,662,168 to Scherbatskoy, U.S. Pat. No. 3,919,479 to Moon, et al., U.S. Pat. No. 4,697,209 to Kiewit, et al., U.S. Pat. No. 4,677,466 to Lert, et al., U.S. Pat. No. 5,512,933 to Wheatley, et al., U.S. Pat. No. 4,955,070 to Welsh, et al., U.S. Pat. No. 4,918,730 to Schulze, U.S. Pat. No. 4,843,562 to Kenyon, et al., U.S. Pat. No. 4,450,551 to Kenyon, et al., U.S. Pat. No. 4,230,990 to Lert, et al., U.S. Pat. No. 5,594,934 to Lu, et al., European Published Patent Application EP 0887958 to Bichsel and PCT publication No. WO 91/11062 to Young, et al., PCT Publication WO 05/006768 to Lee, et al., PCT Publication No. WO 06/023770 to Srinivasan, and PCT Publication No. WO 05/046201 to Lee, all of which are incorporated herein by reference in their entireties.

One advantageous technique carries out either or both of code detection and signature extraction remotely from the location where the research data is gathered, as disclosed in US Published Patent Application 2003/0005430 published Jan. 2, 2003 to Ronald S. Kolessar, which is assigned to the assignee of the present application and is hereby incorporated herein by reference in its entirety.

If location tracking or exposure to outdoor advertising is carried out, then various techniques for doing so are employed. Suitable techniques for location tracking or monitoring exposure to outdoor advertising are disclosed in U.S. Pat. No. 6,958,710 in the names of Jack K. Zhang, Jack C. Crystal, and James M. Jensen, issued Oct. 25, 2005, and US Published Patent Application 2005/0035857 A1 published Feb. 17, 2005 in the names of Jack K. Zhang, Jack C. Crystal, James M. Jensen and Eugene L. Flanagan III, filed Aug. 13, 2003, all of which are assigned to the assignee of the present application and hereby incorporated by reference herein in their entireties.

Where usage of publications, such as periodicals, books, and magazines, is monitored, suitable techniques for doing so are employed, such as those disclosed in U.S. patent application Ser. No. 11/084,481 in the names of James M. Jensen, Jack C. Crystal, Alan R. Neuhauser, Jack Zhang, Daniel W. Pugh, Douglas J. Visnius, and Eugene L. Flanagan III, filed Mar. 18, 2005, which is assigned to the assignee of the present application and hereby incorporated by reference herein in its entirety.

In addition to those types of research data mentioned above and the various techniques identified for gathering such types of data, other types of research data may be gathered and other types of techniques may be employed. For example, research data relating to consumer purchasing conduct, consumer product return conduct, exposure of consumers to products and presence and/or proximity to commercial establishments may be gathered, and various techniques for doing so may be employed. Suitable techniques for gathering data concerning presence and/or proximity to commercial establishments are disclosed in US Published Patent Application 2005/0200476 A1 published Sep. 15, 2005 in the names of David Patrick Forr, James M. Jensen, and Eugene L. Flanagan III, filed Mar. 15, 2004, and in US Published Patent Application 2005/0243784 A1 published Nov. 3, 2005 in the names of Joan Fitzgerald, Jack Crystal, Alan Neuhauser, James M. Jensen, David Patrick Forr, and Eugene L. Flanagan III, filed Mar. 29, 2005. Suitable techniques for gathering data concerning exposure of consumers to products are disclosed in US Published Patent Application 2005/0203798 A1 published Sep. 15, 2005 in the names of James M. Jensen and Eugene L. Flanagan III, filed Mar. 15, 2004.

Moreover, techniques involving the active participation of the panel members may be used in research operations. For example, surveys may be employed where a panel member is asked questions utilizing the panel member's research device after recruitment. Thus, it is to be understood that both the exemplary types of research data to be gathered discussed herein and the exemplary manners of gathering research data as discussed herein are only illustrative and that other types of research data may be gathered and that other techniques for gathering research data may be employed.

Certain research devices, including many disclosed in the patents and applications incorporated herein by reference, are intended solely for use in conducting research operations and do not implement functions of primary benefit to the user. Other research devices are implemented by, in or in combination with a PUA.

Various PUA's already have capabilities sufficient to enable the implementation of the desired monitoring technique or techniques to be employed during the research operation to enable their use as research devices. As an example, cellular telephones have microphones which convert acoustic energy into audio data and GPS receivers for determining their locations. Various cellular telephones further have processing and storage capabilities.

In certain embodiments, various existing PUA's are modified merely by software and/or minor hardware changes to carry out a research operation. In certain other embodiments, PUA's are redesigned and substantially reconstructed for this purpose.

In certain embodiments, the research device itself is operative to gather research data. In certain embodiments, the research device emits data that causes another device to gather research data. Such embodiments include various embodiments disclosed in U.S. Pat. No. 6,958,710 and in U.S. patent application Ser. No. 11/084,481, referenced above, as well as U.S. provisional patent application No. 60/751,825 filed Dec. 20, 2005 assigned to the assignee of the present application and hereby incorporated herein by reference in its entirety. In certain embodiments, the research device is operative both to gather research data and to emit data that causes another device to gather research data.

Figure 1B:
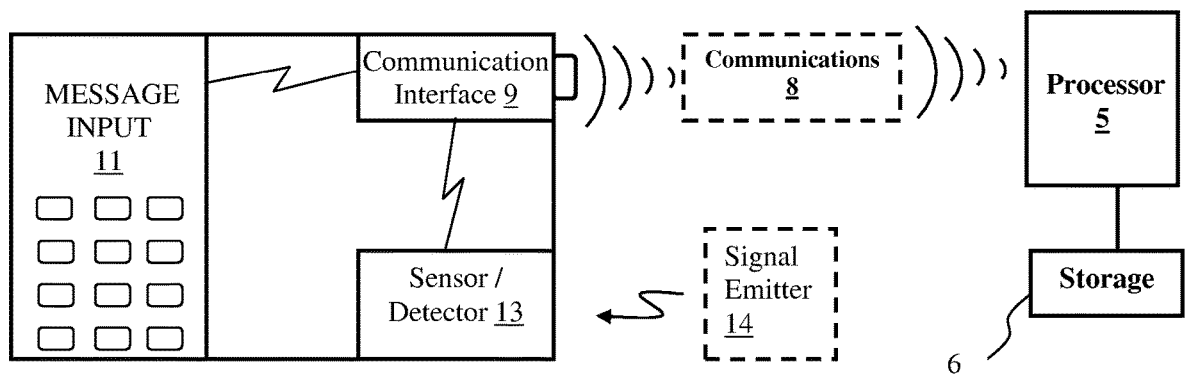
FIG. 1B is a block diagram showing certain details of the monitoring systems of FIG. 1A.

Various embodiments of methods and systems for monitoring use of a research device by one or more users are described herein below. Referring to the drawings, FIGS. 1A and 1B are schematic illustrations of a monitoring system 1 that includes a PUA 2, which is used by a user 3, and a processor 5. In certain embodiments otherwise corresponding to the embodiment of FIGS. 1A and 1B, the PUA 2 is replaced by a research device that does not comprise a PUA. The processor 5 may include one or a plurality of processors which are located together or separate from one another disposed within or controlled by one or more organizations. As shown, the PUA 2 may be coupled to the processor 5 via communications 7 which allows data to be exchanged between the PUA 2 and the processor 5. In certain embodiments, the PUA 2 is wirelessly coupled via communications 7 to the processor 5.

In some embodiments, the monitoring system 1 also includes storage 6 for storing data including, but not limited to, data received and/or processed by the central processor 5. In certain embodiments storage 6 includes one or more storage units located together or separate from one another at the same or different locations. In certain embodiments storage 6 is included with processor 5.

FIG. 1B is a more detailed illustration of an embodiment of the monitoring system 1 in which the PUA 2 is adapted to communicate wirelessly with the processor 5 using wireless communications 8. The PUA 2 includes a communication interface 9 for communicating and receiving data through communications 8. As shown, the PUA 2 also includes a message input 11 to allow the user of the PUA 2 to input a message into the PUA 2. The message input 11 is coupled with the communication interface 9 of the PUA 2, so that a message inputted using the message input 11 can be communicated from the PUA 2 via communications 8. It is understood that messages inputted using the message input 11 may be communicated to the processor 5, or to another PUA 2, or to another location or device coupled with communications 8. In the illustrative embodiment shown in FIG. 1B, the message input 11 comprises a plurality of keys 11 a in the form of a keypad. However, the configuration of the message input 11 may vary, such that, for example, the message input 11 may comprise one or more of a key, a button, a switch, a keyboard, a microphone, a video camera, a touch pad, an accelerometer, a motion detector, a touch screen, a tablet, a scroll-and-click wheel or the like.

In the illustrative configuration shown in FIG. 1B, the PUA 2 also comprises a sensor or a detector 13 for detecting one or more parameters. The parameter or parameters detected by the sensor/detector 13 include, but are not limited to, the remaining power capacity of the PUA 2, one or more of a user's biometric functions or parameters, a location of the PUA 2, a change in location of the PUA 2, data input to the PUA by the user, sounds external to the PUA 2, motion of the PUA 2, pressure being applied to the PUA 2, or an impact of the PUA 2 with another object. In certain embodiments, sensor/detector 13 detects a presence indication signal or a personal identification signal emitted by a signal emitter 14 carried in or on the person of the user. In certain ones of these embodiments, the signal emitter 14 comprises a device worn or carried by the user, such as a ring, a necklace, or other article of jewelry, a wristwatch, a key fob, or article of clothing that emits a predetermined signal indicating a user's presence or the identity of the user wearing or carrying the device. The signal may be emitted as an acoustic signal, an RF or other electromagnetic signal, or a chemical signal that sensor/detector 13 is operative to receive, or an electrical signal. In certain embodiments, the signal emitter 14 comprises a device implanted in the user, such as under the user's skin. In certain embodiments, the sensor/detector 13 includes a plurality of sensors or detectors each for detecting one or more of a plurality of parameters.

As shown in FIG. 1B, the sensor/detector 13 is coupled with the communications interface 9 of the PUA 2 so that data produced as a result of the sensing or detecting performed by the sensor/detector 13 can be communicated from the PUA 2 to the processor 5. Although the PUA 2 shown in FIG. 1B includes both the message input 11 and the sensor/detector 13, it is understood that in other embodiments, one of these elements may be omitted depending on the design of the PUA 2 and the requirements of the monitoring system 1.

As in FIG. 1A, the illustrative configuration of the monitoring system 1 shown in FIG. 1B includes storage 6 coupled or included with the processor 5 to store data, including data received and/or processed by the processor 5. Data stored in storage 6 can also be retrieved by the processor 5 when needed.

Figure 1C:
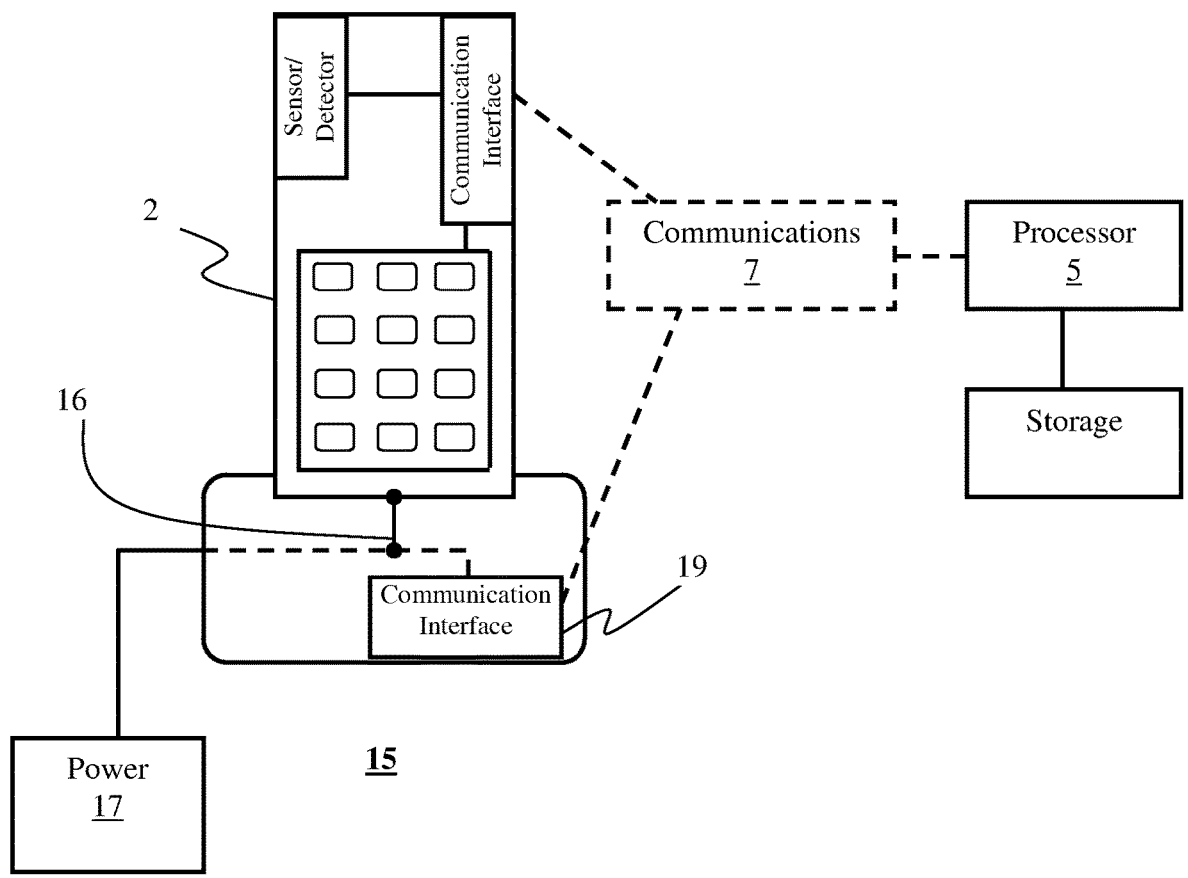
FIG. 1C is a block diagram showing the monitoring systems of FIG. 1A including a PUA coupled with a docking station.

The PUA 2 shown in FIGS. 1A and 1B may be supplied with power from an A/C power source or other power supply, or using one or more batteries or other on-board power source (not shown for purposes of simplicity and clarity). It is understood that batteries used to supply power to the PUA 2 may include any type of batteries, whether rechargeable or not, that are suitable for use with the particular PUA 2. In certain embodiments, the PUA 2 receives power from rechargeable batteries or another kind of rechargeable power supply, such as a capacitor, and/or from a radiant energy converter, such as a photoelectric power converter, or a mechanical energy converter, such as a microelectric generator. In certain embodiments, the PUA 2 is connected with a docking station from time to time, which is used for charging the PUA 2 and/or transmitting data stored in the PUA 2 to the processor 5. FIG. 1C shows an embodiment of the PUA 2 used with the docking station 15. The docking station 15, which is typically not carried by the user and not coupled with the PUA 2 while the PUA is being carried by the user, is adapted to couple with the PUA 2 via a coupling 16. The coupling 16 can be a direct connection between the PUA 2 and the docking station 15 to allow recharging of the PUA 2 and/or communication of data between the PUA 2 and the docking station 15. In certain embodiments, data is communicated from the PUA to the docking station by a wireless infra-red, RF, capacitive or inductive link. In certain embodiments, data is communicated from the PUA 2 to the processor 5 by cellular telephone link or other wired or wireless network or device coupling.

As shown in FIG. 1C, in certain embodiments the docking station is connected to a power supply 17 to provide power for charging the PUA 2 when the PUA 2 is coupled with the docking station 15. In addition, in certain embodiments the docking station 15 includes a communication interface 19 adapted to communicate with the processor 5 through communications 7. When the PUA 2 is coupled with the docking station 15 via the coupling 16, data stored in the PUA 2, such as data collected by the PUA 2 when it was carried by the user, is transferred to the docking station 15 using the coupling 16 and thereafter communicated using the communication interface 19 to the processor 5 through communications 7. In these embodiments, the use of the docking station 15, rather than the PUA 2, to communicate to the processor 5 data collected by the PUA 2 enables conservation of power by the PUA 2 or the use of an internal power supply having a relatively low power capacity. In certain embodiments, the docking station 15 is also used to receive data from the processor 5 via communications 7, and to transfer the received data from the docking station 15 to the PUA 2 via the coupling 16 when the PUA 2 is coupled with the docking station 15.

As can be appreciated, the configuration of the docking station 15 is not limited to the configuration shown in FIG. 1C and may vary from one embodiment to another. For example, in certain embodiments, the docking station is used only for charging the PUA 2 and does not include a communication interface 19. In such embodiments, the docking station 15 is implemented variously as a cradle receiving the PUA 2 or as a standard AC-to DC converter, like a cellular telephone charger. In other embodiments, the docking station 15 is used only for communication of data between the PUA 2 and the processor 5 and does not charge the PUA 2. In such embodiments, the PUA 2 may be connected to a power supply, separate from the docking station 15, for charging, or charged using an internal power converter, or by replacing one or more batteries.

In certain embodiments, the PUA 2 shown in FIGS. 1A-1C optionally includes an output (not shown for purposes of simplicity and clarity) for outputting a message to the user. The output can be in the form of a display for displaying text, or one or more symbols and/or images, a speaker or earphone for outputting a voicemail or a voice message, or one or more LED's or lamps for indicating a message to the user. It is understood that the output or outputs are not limited to the examples provided herein and can comprise any suitable output or outputs adapted to provide a message to the user.

The monitoring system 1 shown in FIGS. 1A and 1B is used for monitoring use by a user of the PUA 2 in accordance with at least one predetermined use criterion. The at least one predetermined use criterion comprises one or more of the following criteria: that the PUA 2 is being carried and/or used, that the PUA 2 is being carried and/or used by a specific user, that the PUA 2 is turned "on," that the PUA 2 is charged, that the PUA 2 maintains a minimum power capacity, that the PUA 2 is, or has been, docked at, or connected with, the docking station 15 for a predetermined length of time, at certain times or during a predetermined time period, that the PUA is functioning properly to provide a benefit to the user, and that the PUA 2 is capable of collecting, storing and/or communicating research data, or of cooperating with one or more other devices to do so.

Other predetermined use criteria not mentioned above may also be employed in monitoring the PUA's use.

In certain embodiments, the method of monitoring use by a user of a research device such as PUA 2 in accordance with at least one predetermined use criterion comprises communicating a request message to the research device, requesting a response from the user of the PUA, receiving a response message communicated from the research device in response to the request message, and storing data indicating whether the use is in compliance with the at least one predetermined use criterion and/or a level of the user's compliance therewith. This monitoring method is illustrated in more detail in FIG. 2A, which shows a block diagram of the actions performed by the monitoring systems shown in FIGS. 1A-1C.

Figure 2A:
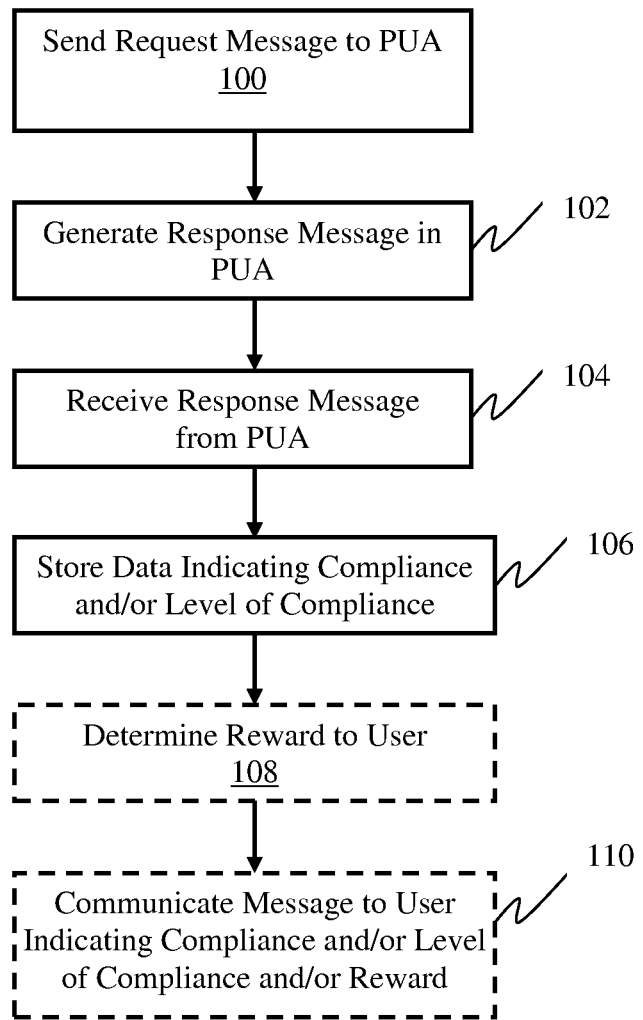
FIGS. 2A and 2B are flow diagrams illustrating actions by the monitoring systems of FIGS. 1A-1C which actively monitor use of the PUA.

As shown in FIG. 2A, a request message is first communicated 100 to a PUA having a two-way communication capability with a remotely-located processor, such as processor 5 of FIGS. 1A-1C, requesting a response from a user of the PUA. In certain embodiments, the request message comprises a text message, a telephone call, a voice mail, an e-mail, a voice message, a sound, a plurality of sounds, a web page, an image, a light alert, or a combination thereof, or any other data presented to the user via the PUA which indicates to the user that a response is being requested. The request message is presented to the user using an appropriate output (for example, a sound reproducing device, such as a speaker or earphone) if the message is a telephone call, a voice mail, a voice message, a sound or a plurality of sounds; a visual display, if the message is a text message, an e-mail, a web page or another image; and/or one or more light emitting devices (for example, LED's or lamps) if the message is a light alert. In certain embodiments, the request message requests a pre-determined response from the PUA user, or a more general response such as a response that acknowledges receipt of the request message. In certain embodiments, the request is accompanied by data of interest to the user, such as access to certain web sites or content, such as music, video, news, or electronic coupons. In certain ones of such embodiments, access to such data is conditioned on providing the requested response according to parameters expressed in the request message or otherwise predetermined. In certain embodiments, the processor is implemented as one or more programmable processors running a communications management program module serving to control communications with the PUA and/or its user, along with other PUA's, to request a response including data from which compliance can be assessed. In certain ones of such embodiments, such communications are scheduled in advance by the programming module with or without reference to a database storing schedule data representing a schedule of such communications, and carried out thereby automatically by means of communications 7. In certain ones of such embodiments, such communications are scheduled in advance and notified to human operators who initiate calls to the PUA's and/or the PUA's users according to the schedule, to solicit data from which compliance can be assessed. In certain ones of such embodiments, both automatic communications and human-initiated communications as described above are carried out.

In response to the request message, a response message is generated 102 in the PUA. In certain embodiments, the response message is generated by inputting the response message by an action of the user using the message input of the PUA. In particular, in certain embodiments in which the response message comprises a code, including letter characters, number characters or symbols, or a combination thereof, the response message is generated using the message input of the PUA. Alternatively, the response message comprises data stored in the PUA, in which case, the response message is generated by selecting the stored data using the message input. In other embodiments, the response message is a response signal generated by activating the message input, such as, for example, by switching one or more switches or by pressing one or more buttons of the message input. Where the response message comprises one or more audible sounds, the response message is generated by inputting the sounds using the message input. In such embodiments, the message input comprises an audio input device, such as an acoustic transducer. As mentioned above, the response message can be generated in response to a request for a pre-determined response, or in response to a request for a more general response.

After the response message is generated in the PUA, the response message is communicated from the PUA through communications thereof and is received 104 in the remotely-located processor, such as processor 5. In certain embodiments, such communications comprises cellular telephone communications, PCS communications, wireless networking communications, satellite communications, or a Bluetooth, ZigBee, electro-optical or other wireless link. In certain embodiments, such communications comprises as Ethernet interface, a telephone modem, a USB port, a Firewire connection, a cable modem, an audio or video connection, or other network or device interface. When the response message from the PUA is received, or a predetermined time period passes without receiving the response message, the processor provides data indicating whether the use of the PUA is in compliance with at least one predetermined criterion and/or the level of the user's compliance. The data provided by the processor is then stored 106 by the processor. In certain embodiments, the processor provides data indicating a user's compliance and/or the level of a user's compliance based on whether or not the response message from the PUA was received. In other embodiments, the processor provides compliance and/or level of compliance data based on the content of the response message, and/or the length of time passed before the response message from the PUA is received, and/or other factors discussed in more detail herein below. In certain embodiments the processor is implemented as one or more programmable processors running a compliance analysis program module which receives the data returned by the PUA and/or the user of the PUA to the communications management program module and serves to analyze the compliance of the user based on such data and in accordance with compliance rules stored in a storage, such as storage 6 of FIGS. 1A-1C. Based on such analysis, the compliance analysis program module produces compliance data indicating whether the user complied with the predetermined use criteria and/or a level of such compliance.

In certain embodiments, a reward may be provided to a user when the user's use of the PUA is in compliance with the predetermined use criteria or when the user's level of compliance is above a pre-selected compliance level. The reward may be in the form of cash, credit, a prize or a benefit, such as a free service or points usable to make purchases or receive prizes, either by means of the PUA or through a different means or service. In certain ones of such embodiments, the reward comprises data of interest to the user, such as access to certain web sites or content, such as music, video, news, or electronic coupons. As shown in FIG. 2A, when data indicating compliance or a level of compliance above a pre-selected compliance level is produced and/or stored, a reward to the user is determined 108. The reward to the user, including the type of the reward and/or an amount or quality of the reward, is determined by the processor of the monitoring system based on the stored data indicating user's compliance or the level of user's compliance. Where the reward is determined based on the level of the user's compliance, in certain embodiments the reward is provided to the user if the user's level of compliance is higher than a predetermined level and/or the type and/or the amount of the reward determined in 108 is varied as the level of the user's compliance increases or decreases. For instance, in certain embodiments a number of points awarded to the user that may be used to purchase goods or services, is greater where the user responds to a larger percentage of request messages, or is increased as the number of request messages that the user responds to increases.

Providing rewards to PUA users for use of the PUA in compliance with the predetermined use criteria provides an incentive for the users to comply with the use requirements so as to earn a reward or to earn a higher reward. Therefore, providing a reward to the PUA user for the correct use of the PUA also promotes correct use of the PUA in the future in accordance with the predetermined usage criterion or criteria.

In certain embodiments, the monitoring system also communicates a message to the PUA user indicating compliance and/or the level of compliance with the predetermined use criteria for the PUA and/or the reward earned by the user 110. The message communicated to the user can be in the form of a text message, a telephone call, a voice mail, a voice message, an e-mail, an image or a combination thereof communicated via the PUA or otherwise. In some embodiments, the message can be in form of a light indication, such as by lighting up an LED or lamp to indicate whether the use of the PUA is in compliance or whether a reward has been earned by the user. As shown in FIG. 2A, the determination of the reward to the user 108 and the communication of the message to the user 110 are optional actions by the monitoring system in monitoring the user's use of the PUA. In some configurations, for example, the determination of the reward is omitted and the monitoring system proceeds to communicating the message to the user indicating the user's compliance and/or level of compliance. In other configurations, however, the monitoring system determines the reward to the user and automatically provides the reward to the user, such as by sending the reward directly to the user or applying the reward to the user's account, without communicating any messages to the user indicating the user's compliance, level of compliance or reward earned. In certain embodiments, where the monitoring system has determined that a user has failed to comply, it sends one or more messages to the user and/or to the user's PUA noting such failure, with or without further message content encouraging compliance in the future. In certain ones of such embodiments, the message noting failure to comply is sent in a plurality of different forms, such as both a text message and a voice call, which can be generated either automatically or by human intervention. In certain embodiments, the determination of a reward is made by one or more programmable processors running a reward determination program module that receives the compliance data produced by the compliance analysis program module and serve to produce reward data based on stored rules, such as rules stored in storage 6, specifying what rewards (including kind and amount), if any, to accord to the user for whom the compliance data was produced. Based on the reward data, the communications management program module communicates a reward notification to the PUA and/or its user, and/or communicates an order to a service (such as a supplier of goods or services, which can include content and other data) to provide the determined rewards to the user or credit an account of the user with such rewards.

Figure 2B:
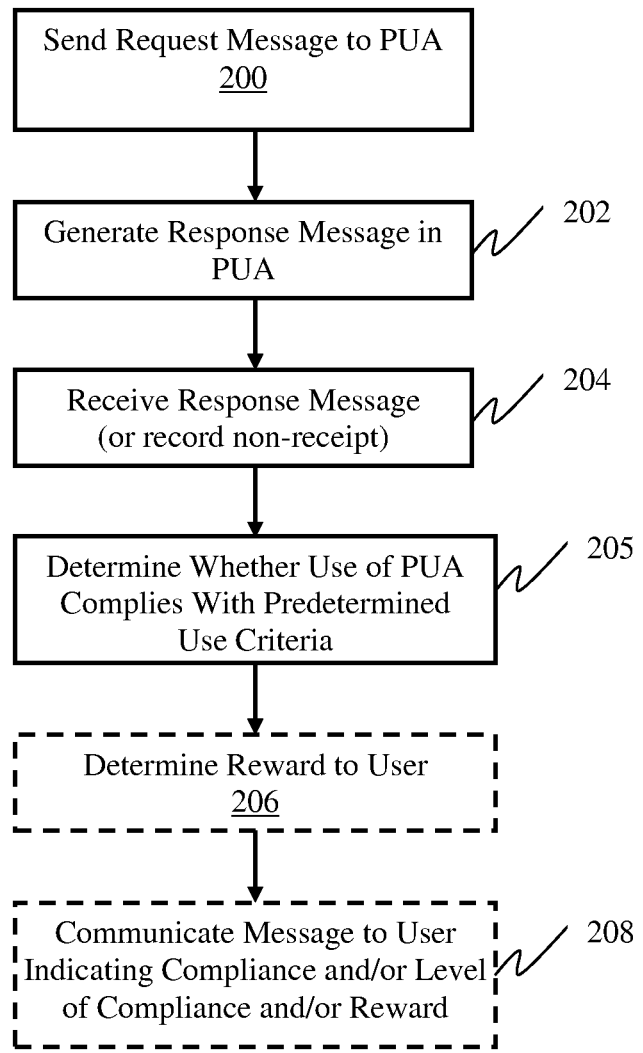

In certain embodiments, the use of a research device is monitored by communicating a request message to the research device, the request message requesting a response from the user of the research device, receiving a response message communicated from the research device in response to the request message, and determining whether the use of the research device by the user is in compliance with the at least one predetermined use criterion. FIG. 2B illustrates this embodiment of monitoring use of a research device, namely, a user's PUA, by the monitoring system. In certain other embodiments otherwise corresponding to the embodiment of FIG. 2B, the user's PUA is replaced by a research device that does not comprise a PUA.

As shown in FIG. 2B at 200, a request message is sent to a PUA from a monitoring system, a response message is generated 202 in the PUA and communicated thereby to the monitoring system, in response to the request message and the response message is received 204 by the monitoring system from the PUA (or its non-receipt is recorded). These actions performed by the monitoring system are similar to those, i.e. 100, 102 and 104, described above with respect to FIG. 2A, and therefore a detailed description thereof is omitted for purposes of clarity and simplicity. As further shown in FIG. 2B, when the response message is received from the PUA, the monitoring system determines 205 whether the user's use of the PUA complies with at least one predetermined use criterion. This determination 205 is performed by a processor of the monitoring system. As mentioned herein above, the predetermined criteria includes, but is not limited to, the PUA being carried, the PUA being carried by a specific user, the PUA being turned "on," the PUA being charged, the PUA maintaining a minimum charge or power capacity, the PUA being docked at, or connected with, the docking station for a predetermined length and/or period of time, or at certain times, the PUA functioning properly and the PUA being capable of collecting, storing and/or communicating research data, or of cooperating with one or more other devices to do so.

In certain embodiments, the determination 205 whether the use of the PUA is in compliance with the predetermined criteria is based on at least one of the receipt or non-receipt 204 of the response message from the PUA, the time of receipt of the response message and the content of the response message. For example, when the determination 205 is based on the receipt or non-receipt of the response message from the PUA, the processor determines that the use of the PUA is not in compliance with the predetermined criteria if the receipt message is not received within a predetermined period of time from the sending of the request message to the PUA in 200. In certain ones of such embodiments, a request message requesting a response from the user (such as a text message or voice prompt) is sent to the PUA at regular intervals during the day, at intervals determined according to dayparts or according to a pseudorandom schedule, and the promptness of the user's response, if any, is used to determine an amount or quality of a reward to the user.

When the determination of compliance with predetermined use criteria is based on the time of receipt of the response message, the processor determines how much time had elapsed between the time of sending of the request message to the PUA and the time of receipt of the response message from the PUA and compares it to a selected compliant response time. The compliant response time in certain embodiments is a constant duration for all users, all PUA's, all types of request messages, all places and all times. In certain other embodiments, the compliant response time is selected based on user demographics or an individual profile. In certain embodiments, the compliant response time is based on the type of request message and/or its contents. In certain ones of such embodiments, the compliant response time is specified in the message, for example, "Please respond within ten minutes." In certain embodiments the compliant response time is selected based on the type of PUA that receives it, for example, a cellular telephone or Blackberry device for which a relatively short response time can be expected, as compared to a personal audio or DVD player, for which a longer response time may be appropriate. In certain embodiments, the compliant response time is selected depending on the manner in which the request message is to be presented to the user. For example, if receipt of the message is indicated to the user by an audible alert or device vibration, a shorter response time can be expected than in the case of a message presented only visually. In certain embodiments, the compliant response time is selected based on the time of day. For example, during morning or afternoon drive time, the response time may be lengthened since the user may not be able to respond as quickly as during the evening when the user is at home. In certain embodiments, the compliant response time is selected based on the user's location. For example, in certain places it may be customary to respond to messages more quickly than in others. In certain embodiments, the compliant response time is selected based on a combination of two or more of the foregoing factors.

If the time elapsed between the sending of the request message and the receipt of the response is less than the selected response time, it is determined that the user's use of the PUA is in compliance with the pre-determined criteria. However, if the elapsed time is greater than the selected response time, it is determined that the use of the PUA is not in compliance with the predetermined criteria. In certain embodiments, the amount of time elapsed between the sending 200 of the request message and the receiving 204 of the response message is used to determine a level of the user's compliance with the predetermined use criteria. In particular, the level of compliance determined by the processor will depend on how quickly the response message is received by the processor, such that the level of compliance is greater as the amount of time elapsed between the sending 200 of the request message and the receipt 204 of the response message is less.

When the determination whether the user's PUA use is in compliance with one or more predetermined criteria is based on the content of the response message, the processor determines whether the content of the response message complies with predetermined parameters. In such embodiments, a selected response message, complying with predetermined parameters, is requested 200 by the request message communicated to the PUA, and in determining compliance and/or the level of compliance, the processor compares the response message received 204 from the PUA with the requested response. In one illustrative embodiment, the request message communicated 200 to the PUA comprises a request for the user's password or for a particular code, such as a user' screen name or real name, and the response message received 204 in response to the request message is compared by the processor to pre-stored data, such as a password, code, screen name or real name stored in a database, to determine 205 whether the use of the PUA is in compliance with the predetermined criteria. If the received response message matches the stored message, i.e. password, a name (such as a screen name selected by the user or the user's real name) or a code, stored in the database, then the processor determines that the user is in compliance with the predetermined criteria. By requesting a selected response message, such as a password, name or code, the monitoring system is capable not only of confirming that the PUA is being carried and/or used, but also of confirming that the PUA is being carried and/or used by a specific user.

In certain embodiments, in addition to or instead of other requested information, the requested response comprises information from the user, such as what the user is doing when the message is received or at other times, the user's location or locations at various times, media or products to which the user has been exposed, has purchased or used, or plans to purchase or use, the user's beliefs and/or the user's opinions. In certain embodiments, in addition to or instead of other requested information, the requested response comprises information concerning an operational state of the PUA (for example, as indicated thereby or as determined by the user), whether and/or when the user performed some action (such as docking or recharging the PUA), and/or whether and/or how the user is carrying the PUA.

In certain embodiments, the processor determines 205 the level of the PUA user's compliance based on the content of the message. In this illustrative embodiment, the response message received 204 is compared with stored data, such as a password, name or code stored in the database, and determines the level of compliance based on how closely the response message matches with the stored data. In certain ones of such embodiments, a first, or highest, level of compliance is determined if the response message matches the stored message, a second level of compliance, which is lower than the first level, is determined if the response message does not match the stored message, and a third, or lowest, level of compliance is determined if no response message is received 204 from the PUA. In some embodiments, a plurality of different intermediate levels of compliance may be determined instead of the second level of compliance, if a response message is received but does not match the stored message. In such embodiments, the level determined is based on the extent of similarity between the response message and the pre-stored data. Thus, for example, the intermediate level of compliance will be higher in a case where the response message received 204 from the PUA differs from the stored message by only one character than in a case where the response message received from the PUA is completely different from the stored message.

In certain embodiments, the user's compliance and/or level of compliance is determined not only based on the content of the response message but also on the time of receipt of the response message. In certain ones of such embodiments, the user's compliance will depend on whether the response message matches with the stored data, as well as on how quickly the response message is received from the PUA. In certain ones of such embodiments, the highest level of compliance is determined if the response message received from the PUA matches the stored data, and if the time elapsed between the sending of the request message to the PUA and the receipt of the response message is less than a selected time. If the response message does not match the stored data and/or the time elapsed between the sending of the request message and the receipt of the response message is greater than the selected time, then the level of compliance determined 205 is selected at a level intermediate a highest level of compliance and a lowest level. If no response message is received from the PUA, then the lowest level of compliance, or non-compliance is determined by the monitoring system.

In some embodiments, the monitoring system also determines and/or provides 206 a reward to the user for complying with predetermined criteria 206 and/or sends a message to the user indicating at least one of the user's compliance, the level of compliance and the reward to the user 208. In particular, after the monitoring system determines whether the PUA use complies with the predetermined use criteria and/or the level of the user's compliance, the monitoring system proceeds to determine and/or provide 206 a reward to the user of the PUA. The system then communicates 208 a message to the user indicating the user's compliance, level of compliance and/or the reward earned by the user. These actions performed by the monitoring system are similar to those (106 and 108) described above with respect to FIG. 2A, and thus a detailed description thereof is omitted. As in the embodiments described with respect to FIG. 2A, the determination and/or provision 206 of the reward and the communication 208 of the message indicating compliance, level of compliance and/or the reward are optional. Moreover, as in the embodiments described with respect to FIG. 2A, in certain embodiments, the determination and/or provision of the reward is performed without communicating the message to the user, while in other embodiments, the communication 208 of the message is performed without determining and/or providing 206 the reward.

Figure 3A:
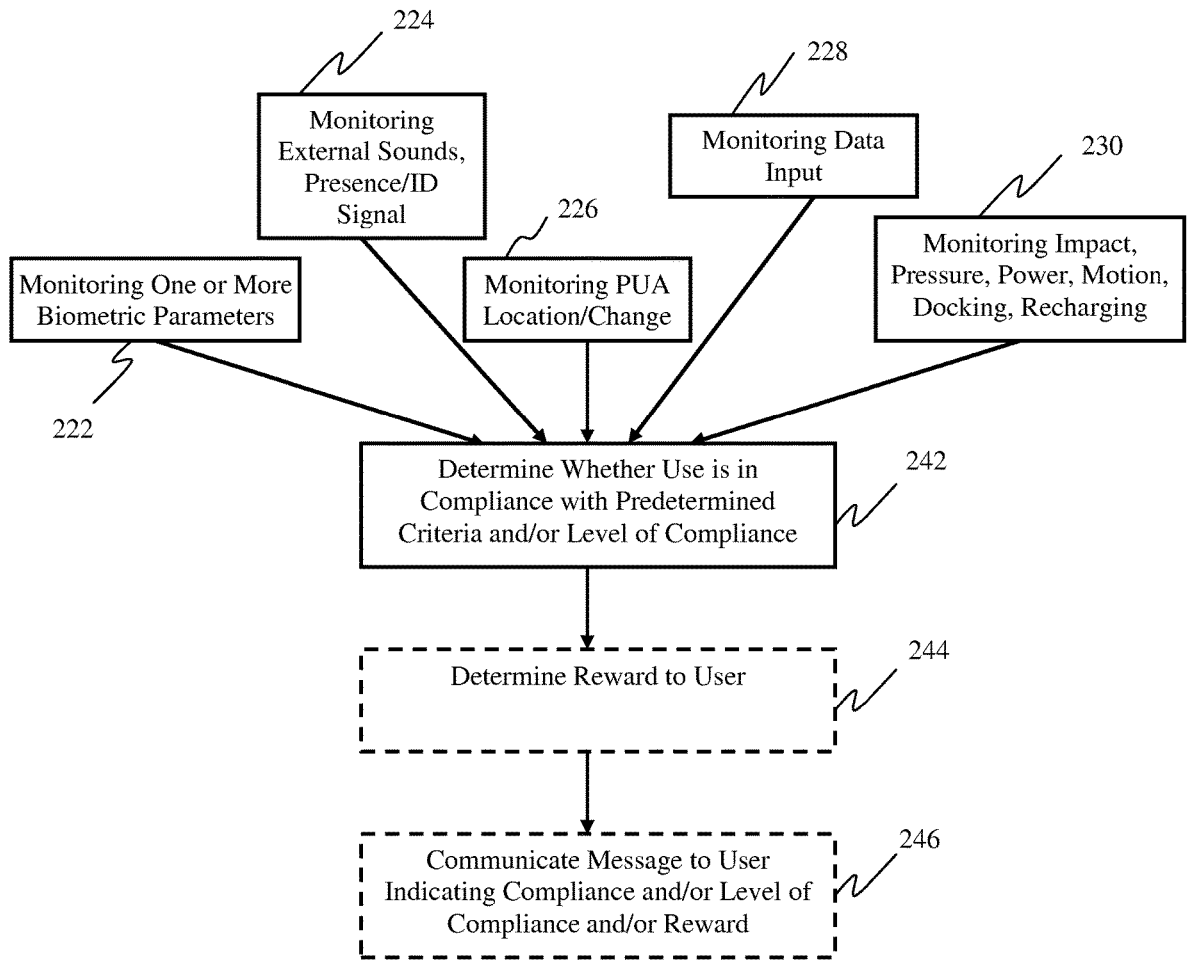
FIGS. 3A and 3B are flow diagrams illustrating actions by the monitoring systems of FIGS. 1A-1C which passively monitor use of the PUA.

In certain embodiments of monitoring methods and systems, the monitoring system monitors one or more parameters, such as biometric parameters, sounds external to a research device, an impact of the research device with another object, motion of the research device, proximity of the research device to the person of a user, proximity of the research device to a presence indicator or personal identification device in or on the person of a user, pressure applied to the research device, recharging of the research device, its power capacity, docking of the research device, data input (e.g., messages) to the research device, location of the research device and/or changes in the research device's location, to determine whether the use of the research device is in compliance with at least one predetermined criterion. In one illustrative embodiment, the monitoring system produces monitored data by monitoring at least one of a user's heart activity, a user's brain activity, a user's breathing activity, a user's pulse, a user's blood oxygenation, a user's borborygmus (gastrointestinal noise), a user's gait, a user's voice, a user's key, keypad or keyboard usage characteristics (e.g., keystroke recognition), a user's vascular pattern, a user's facial or ear patterns, a user's signature, a user's fingerprint, a user's handprint or hand geometry, a user's retinal or iris patterns, a user's airborne biochemical indicators (sometimes referred to as a user's "smellprint"), a user's muscular activity, a user's body temperature, sounds external to the research device, motion of the research device, pressure applied to the research device, recharging of the research device, docking of the research device, its power capacity, an impact of the research device with another object, data input to the research device by a user, location of the research device and a change in a location of the research device, and determines whether use of the research device by the user is in accordance with at least one predetermined criterion based on the monitored data. The operations of the monitoring system in these illustrative embodiments to monitor use of a PUA are shown in FIG. 3A. It will be appreciated that the embodiment of FIG. 3A is also applicable to a research device that is not a PUA.

As shown in FIG. 3A, at least one of a biometric parameter 222, proximity of the PUA to the person of a user, proximity of the PUA to a presence indicator or personal identification device in or on the person of the user, external sounds 224, PUA location, PUA location change 226, data input 228 and impact of the PUA with another object, pressure applied to the PUA, power capacity, motion, recharging, docking 230 are monitored to produce monitored data. When one or more biometric parameters is monitored 222, these parameters include, but are not limited to, one or more of the user's heart activity, the user's brain activity, the user's breathing activity, the user's pulse, the user's blood oxygenation, the user's borborygmus, the user's gait, the user's key, keypad or keyboard usage characteristics, the user's voice, the user's fingerprint, the user's handprint or hand geometry, the user's retinal or iris patterns, the user's smellprint, a vascular pattern of the user, the user's facial or ear patterns, a pattern of muscle activity of the user, the user's signature, and the user's body temperature.

Referring again to FIG. 1B, the monitoring of the biometric parameters 222, external sounds, presence indication signal, personal identification signal 224, PUA location, PUA location changes 226, data input 228 and/or impact of the PUA with another object, pressure applied to the PUA, motion of the PUA, recharging, power capacity, docking 230 is performed in the PUA 2 by the sensor/detector 13 in cooperation with a processor of the PUA (not shown for purposes of simplicity and clarity). As mentioned above, the sensor/detector 13 in certain embodiments includes a plurality of sensors and/or detectors which monitor a plurality of parameters. In the embodiments in which the sensor/detector 13 monitors one or more biometric parameters of the PUA user 222, the sensor/detector 13 comprises one or more of a heart monitor for monitoring heart activity of the user, an EEG monitor for monitoring the user's brain activity, a breathing monitor for monitoring the user's breathing activity including, but not limited to, the user's breathing rate, a pulse rate monitor, a pulse oximeter, a sound detector for monitoring the user's borborygmus and/or the user's voice, a gait sensor and/or a gait analyzer for detecting data representing the user's gait, such as a motion sensor or accelerometer (which may also be used to monitor muscle activity), a video camera for use in detecting motion based on changes to its output image signal over time, a temperature sensor for monitoring the user's temperature, an electrode or electrodes for picking up EKG and/or EEG signals, and a fingerprint or handprint scanner for detecting the user's fingerprint or handprint. Where the user's retinal or iris patterns are monitored, sensor/detector 13 comprises a low-intensity light source, for scanning, detecting or otherwise sensing the retinal or iris patterns of the user. Where the user's hand geometry is detected, sensor/detector 13 comprises a device configured with an optical sensor or other imaging device to capture predetermined parameters of the user's hand, such as hand shape, finger length, finger thickness, finger curvature and/or any portion thereof. Where the user's smellprint is detected, sensor/detector 13 comprises an electronic sensor, a chemical sensor, and/or an electronic or chemical sensor configured as an array of chemical sensors, wherein each chemical sensor may detect a specific odorant or other biochemical indicator. Where a vascular pattern of the user is detected, sensor/detector 13 comprises an optical or other radiant energy scanning or imaging device for detecting a vascular pattern or other tissue structure, or blood flow or pressure characteristic of the user's hand or other body part. Where the user's facial or ear patterns are detected, the sensor/detector 13 comprises a video camera, optical scanner or other device sufficient to recognize one or more facial features or one or more features of the user's ear or other body part. In certain ones of these embodiments, the sensor/detector 13 is mounted in or on the PUA 2, while in others the sensor/detector 13 is arranged separately from the PUA 2 and communicates therewith via a cable or via an RF, inductive, acoustic, infrared or other wireless link.

In the embodiments in which the sensor/detector 13 of the PUA 2 monitors sounds external to the PUA 224, the sensor/detector 13 comprises an acoustic sensor such as a microphone or any other suitable sound detector for detecting external sounds. In certain embodiments, the sensor/detector 13, which monitors external sounds, cooperates with the processor for analyzing the detected external sounds. The external sounds detected by the sensor/detector 13 include, but are not limited to, environmental noise, rubbing of the PUA 2 against the user's clothing or other external objects, vehicle sounds (such as engine noise and sounds characteristic of opening and closing car doors), the user's voice print, dropping of the PUA, average ambient noise level, and the like. In the embodiments in which sensor/detector 13 receives a presence indication signal or personal identification signal from signal emitter 14, sensor/detector 13 comprises a device operative to receive the signal, such as an RF receiver, a microphone, an optical sensor, an inductive pickup, a capacitive pickup, a chemical sensor or a conductive connection.

In certain ones of the embodiments in which the sensor/detector 13 monitors the user's data input 228 (e.g., messages or inputs to control a diverse operation of the PUA, such as to make use of an application running thereon, like a game), the sensor/detector 13 comprises a pressure sensor for sensing pressure applied to the message input by the user. Alternatively or in addition, the sensor/detector 13 comprises a utility, such as a key logger, running on the processor of the PUA to determine and record its usage.

In the embodiments in which location change is being monitored 226, the sensor/detector 13 directly or indirectly detects the change in the PUA's location. Direct detection of the PUA's location is accomplished by detecting the location of the PUA and the change in PUA's location over time. In this case, the sensor/detector 13 comprises a satellite location system, such as a GPS receiver, an ultra wideband location detector, a cellular telephone location detector, an angle of arrival location detector, a time difference of arrival location detector, an enhanced signal strength location detector, a location fingerprinting location detector, an inertial location monitor, a short range location signal receiver or any other suitable location detector. The same means can also be employed to determine the PUA's location. Indirect detection of the PUA's location change is accomplished by detecting a predetermined parameter which is directly or indirectly related to the location of the PUA and determining from variations in the predetermined parameter whether a change in the location of the PUA has occurred. One of such predetermined parameters detected by the sensor/detector 13 can be variations in the strength of a RF signal received by the PUA, and in such case, the sensor/detector 13 comprises a RF signal receiver. Where location change data is available such data is used in certain embodiments to determine whether and when the PUA was or is being carried.

In embodiments in which the sensor/detector 13 monitors the impact of the PUA 2 with another object 230, the sensor/detector 13 comprises an impact detector for measuring pre-determined levels of impact of the PUA 2 with other objects. In certain embodiments, the sensor/detector 13 comprises an accelerometer for detecting a relatively large acceleration upon impact of the PUA 2 with another object.

In embodiments where pressure applied to the PUA is monitored, a pressure sensor is placed on an enclosure of the PUA or mechanically coupled therewith to receive force applied to such enclosure. In certain ones of such embodiments, the magnitude of the pressure as it varies over time and/or with location on the enclosure are analyzed to determine if the PUA is being or was carried and/or the manner in which it was used and/or the event of non-use.

In certain embodiments where motion of the PUA is monitored, a video camera of the PUA is used as a motion sensor. In certain ones of such embodiments, changes in the image data provided at the output of the video camera (either the entire image or one or more portions thereof) are processed to determine movement or an extent of movement of the image over time to detect that the PUA is being moved about, either by translation or rotation. Techniques for producing motion vectors indicating motion of an image or an extent of such motion are well known in the art, and are used in certain embodiments herein to evaluate whether the PUA is moving and/or the extent of such movement. In certain ones of such embodiments, changes in the light intensity or color composition of the image data output by the video camera (either the entire image or one or more portions thereof) over time are used to detect motion of the PUA. In certain embodiments where motion of the PUA is monitored, a light sensitive device, such as a light sensitive diode of the PUA, is used as a motion sensor. Changes in the output of the light sensitive device over time that characterize movement serve to indicate that the PUA is being carried.

In certain embodiments, the one or more parameters also include power remaining in the PUA, recharging of the PUA and/or the event of docking of the PUA by coupling the PUA with the docking station, for example, as illustrated in FIG. 10. In such embodiments, the monitoring system produces monitored data by monitoring the power remaining in the PUA and/or by monitoring the docking of the PUA at the docking station. In the embodiments in which the docking of the PUA is monitored, the monitoring system monitors the length of time the PUA was coupled with the docking station, the time period during which the PUA was coupled with the docking station, a time at which the PUA is docked, a time at which the PUA was undocked, whether or not the PUA is coupled with the docking station and/or the length of time passed since the PUA was last docked at the docking station.

The monitoring of one or more parameters 222-230 by the monitoring system, as described above, produces monitored data which indicates at least whether or not the PUA was being carried and/or used in one or more of various ways. For example, if monitoring includes monitoring one or more biometric parameters of the user, then the monitored data indicates at least whether or not the biometric parameters being monitored have been detected. Similarly, in the case of monitoring PUA location changes, external sounds, data input, pressure, motion, light changes and/or impact of the PUA with other objects, the monitored data includes data indicating at least whether or not any of these parameters have been detected. Monitored data that indicates that one or more of these parameters have been detected in the PUA, in turn, indicates that the PUA was being carried and/or used, while monitored data indicating a lack of any detection of one or more of the monitored parameters indicates that the PUA was not being carried or used.

In certain embodiments, the monitored data produced indicates at least whether or not the PUA was charged and/or whether or not the PUA was docked at the docking station according to a predetermined time parameter. In the case of monitoring the power charge in the PUA, the monitored data includes data indicating at least whether or not the PUA was charged, and in certain embodiments, the monitored data indicates whether the power capacity remaining in the PUA was greater than a predetermined minimum. Where monitoring includes monitoring of the docking of the PUA at the docking station, the monitored data indicates at least whether or not the PUA was docked at the docking station at any time, and in some embodiments, the monitoring data indicates one or more of whether or not the PUA was docked at the docking station for a predetermined length of time, how frequently the PUA was docked, when the PUA was docked, when the PUA was undocked and/or the time periods during which the PUA was docked. The monitored data produced in these embodiments can be used to determine whether the use of the PUA was in compliance with the criteria for recharging of the PUA and/or docking of the PUA.

In certain embodiments, monitored data comprises data which can be used to confirm the identity of the PUA user. For example, if one or more biometric parameters of the user are monitored by the sensor/detector, the monitored data includes data indicating or relating to one or more of the user's heart rate or other heart activity or parameter, EEG, blood oxygenation, breathing rate or other breathing activity or parameter, borborygmus, gait, voice, voice analysis, key, keypad or keyboard usage characteristics, fingerprints, handprints, hand geometry, pulse, retinal or iris patterns, olfactory characteristics or other biochemical indicators, patterns of muscular activity, vascular patterns, facial or ear patterns, signature, and/or body temperature detected once or a plurality of times over a predetermined period of time. In certain embodiments, the user is identified by a signal from signal emitter 14. In another example, if the PUA location change is being monitored, then monitored data can include data relating to the specific locations or changes in location of the PUA and/or relating to the specific RF signal strengths of the PUA detected one or a plurality of times over a predetermined period of time.

Referring now back to FIG. 3A, the monitored data produced by monitoring at least one of a user's biometric parameters, external sounds, PUA location or location change, data input, pressure applied to the PUA, impact of a PUA with another object, a signal from signal emitter 14, PUA motion, PUA power level, recharging and docking of the PUA at the docking station is used to determine whether the user's use of the PUA is in compliance with the predetermined criteria and/or the user's level of compliance 242. In certain embodiments, the determination of compliance and/or level of compliance is performed in the PUA by its processor, while in other embodiments, the monitored data produced in the PUA is communicated to the processor 5 via its communications and the processor 5 then determines the user's compliance and/or level of compliance.

In certain embodiments, the determination of compliance and/or level of compliance is performed based on the detection or non-detection of one or more monitored parameters, as indicated by monitored data, to determine whether the PUA was carried and/or was charged at the monitoring times and/or whether the PUA was docked and/or undocked at predetermined times or time periods. In certain embodiments in which, as mentioned above, monitored data includes more specific or extensive data, the determination of compliance and/or level of compliance includes not only a determination whether the PUA was carried but also a confirmation that the PUA was carried by a specific user. In such embodiments, the compliance determination is performed by comparing the monitored data with pre-stored data relating to the specific user to determine whether the PUA was carried and whether the user carrying the PUA was the specific user. In particular, if the monitored data corresponds to the stored data for the specific user, then it is determined that the user carrying the PUA was the specific user. However, if the monitored data does not correspond to the stored data for the specific user, then it is determined that the user carrying the PUA was not the specific user. The determination whether the PUA use is in compliance with the predetermined criteria and/or the determination of the level of the user's compliance is then based on the determinations whether the PUA was carried and whether the user carrying the PUA was the specific user.

In certain embodiments, the PUA use is determined to be in compliance with the predetermined criteria if it is determined that the PUA was carried by the specific user and not in compliance if it is determined that the PUA was not carried. Depending on requirements of the monitoring systems and the predetermined criteria, in some embodiments the PUA use is determined to be in compliance, or in partial compliance, if it is determined that the PUA was carried by someone other than the specific user. However, in other embodiments, the monitoring system determines that the PUA use does not comply with the predetermined criteria if it is determined that the PUA was carried by someone other than the specific user.

With respect to the determination of the level of compliance, in certain embodiments, the highest level of compliance is determined if it is determined that the PUA was being carried by the specific user and the lowest level of compliance is determined if it is determined that the PUA was not carried. In certain embodiments, if the PUA was carried by someone other than the specific user at all or some of the monitoring times, then an intermediate level of compliance that is lower than the highest level and higher than the lowest level is determined. The value of the intermediate compliance level may depend on whether the PUA was carried by someone other than the specific user at all or some of the times and the number of times that it is determined that the PUA was carried by someone other than the specific user, if a plurality of determinations are made.

As shown in FIG. 3A, the user of the PUA may optionally be rewarded for the user's compliance with the predetermined use criteria. As discussed above, providing a reward to the user in return for the compliant use of the PUA provides an incentive for the user to comply with the PUA use requirements in the future. In the embodiments where the monitoring system provides a reward to the user, the reward to the user is determined 244 after the determination of compliance and/or level of compliance 242 is made. The determination of the reward is based on whether the user has complied with the predetermined use criteria and/or based on the level of user's compliance, and can be performed in the PUA or in the processor. As mentioned above with respect to FIGS. 2A and 2B, the reward to the user can include cash, credit, points usable to make purchases, services or other benefit to the user.

As also shown in FIG. 3A, in certain embodiments, the monitoring system optionally communicates a message to the PUA user indicating compliance and/or level of compliance and/or a reward earned by the user 246. In these embodiments, the message can be in the form of a telephone call, a text message, a voice mail, a voice message, an image, an email, a web page, a paper notification or any other suitable indication to the user. In certain ones of such embodiments, a light is illuminated or blinks, or a sound is emitted (similar to a voice mail notification) at intervals (such as an interval from one to five minutes) to indicate compliance or non-compliance. Where the light or sound notification indicates non-compliance, its intensity and/or frequency increases over time to gain the user's attention. Referring now to FIG. 1B, if the determination of compliance, level of compliance and/or reward is performed by the processor of the PUA, the message indicating compliance, level of compliance and/or reward can be communicated to the user by the PUA. If, on the other hand, the determination of compliance, level of compliance and/or reward is performed by the processor 5, the message can be communicated to the PUA to provide the message to the user, or the message can be communicated to the user by another means.

As discussed above, the determination of a reward to the user 244 and the communication of a message to the user 246 are optional. Thus, it is understood that the monitoring system may perform both, none or only one of these actions, depending on the arrangement of the PUA and the requirements of the monitoring system.

Figure 3B:
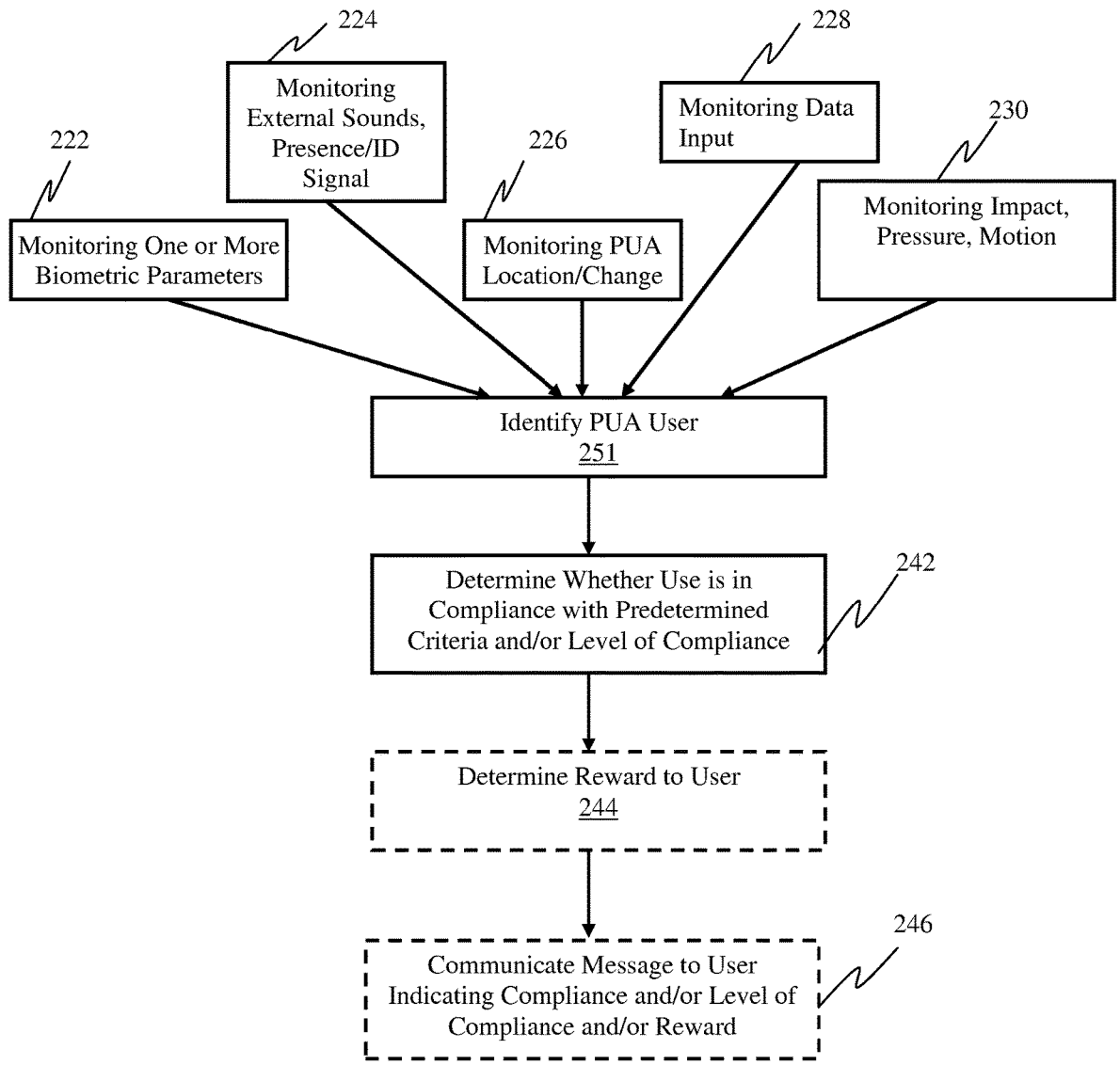

In certain other embodiments, methods and systems for monitoring use by a user of a research device comprise producing monitored data by monitoring one or more parameters, producing identification data identifying the user based on the monitored data and determining, based on the identification data, whether the research device is being used by the user in accordance with at least one predetermined use criterion. FIG. 3B illustrates the actions performed by the monitoring system of this embodiment wherein the research device comprises a PUA, but it will be appreciated the monitoring system is also applicable to embodiments in which the research device does not comprise a PUA. In FIG. 3B, actions performed by the monitoring system similar to those illustrated in FIG. 3A are indicated by the same reference numbers as in FIG. 3A.

As shown in FIG. 3B, the monitoring system monitors at least one of a user's biometric parameter 222, external sounds, a presence indication signal, a personal identification signal 224, PUA location, PUA location change 226, data input to the PUA 228 and impact of the PUA with another object, motion of the PUA, pressure applied to the PUA 230. As discussed herein above with respect to FIG. 3A and referring to FIG. 1B, the monitoring is performed by the sensor/detector 13 in the PUA 2, and as a result of this monitoring, monitored data relating to the parameters monitored is provided. In certain ones of these embodiments, the monitor stores one or more signatures, feature sets or other characteristic data of the panelist assigned to the PUA (and thus the person who should be its sole user) to which the monitored data is compared to determine if the data match. This comparison provides an indication whether the PUA in fact is being carried and/or used by the correct user. If, for example, the monitoring system monitors the sounds external to the PUA, the monitored data will include not only an indication that an external sound was detected, but also data relating to the sound that was detected, such as analysis of the detected sound, the frequency of the detected sound, voice identification data and/or other data relating to the detected sound, from which a sound signature or feature set can be produced for comparison against a stored signature or feature set to assess whether the PUA is in the possession of the correct user. In certain embodiments, the monitored data is used to determine whether the PUA is being carried. Thus, for example, if the monitoring system monitors the location change of the PUA, the monitored data will include data not only indicating a change in the PUA's location, it may be inferred that the monitor is in the possession of a user who is carrying it about.

Referring to FIG. 3B, the monitored data produced by monitoring one or more of the above-mentioned parameters is used to provide identification data which is, in turn, used to identify the user of the PUA 251. In certain embodiments, the identification data is provided by the PUA and/or the docking station, while in other embodiments, the monitored data is communicated from the PUA to the processor 5 via the communications and the processor 5 provides the identification data based on the monitored data. In certain embodiments, the identification data is provided by comparing the monitored data with pre-stored data relating to at least one PUA user so as to determine the identity of the PUA user and/or to confirm that the PUA user is the specific user corresponding to the pre-stored data. The pre-stored data may be based on data relating to the PUA user obtained from the specific user in advance, or may be based on previously collected monitored data. By providing the identification data relating to the identity of the user, the monitoring system is adapted to confirm that a specific person, and not someone else, is carrying and/or using the PUA.

When the identification data is produced in 251, the monitoring system determines whether the use of the PUA is in compliance with at least one predetermined use criterion and/or the level of the user's compliance 242. This determination 242 is made based on the identification data identifying the user. In some embodiments, in which the identification data indicates that the person carrying and/or using the PUA is the corresponding, or correct, PUA user, the monitoring system determines in 242 that the PUA user has complied with at least one predetermined use criterion. The level of the user's compliance can be determined based on whether or not the PUA was carried and/or used in accordance with the predetermined criteria and based on whether or not identification data indicates that the person carrying and/or using the PUA matches the corresponding user for the PUA, as well as based on the frequency of compliant use indications. Thus, for example, a first level of compliance is determined if the identification data indicates that the PUA was carried by the user corresponding to the specific user for the PUA, a second level of compliance which is lower than the first level of compliance is determined if the identification data indicates that the PUA was carried by a user who does not correspond to the specific user of the PUA and a third level of compliance, which is lower than both the first and the second levels, is determined if the identification data indicates that the PUA was not carried by any user. It is understood that these compliance levels are illustrative and that the number of levels and how these levels are determined may vary.

As in FIG. 3A, in certain embodiments, the monitoring system provides a reward to the user for complying with the predetermined criteria 244 and/or sends a message to the user indicating at least one of compliance, level of compliance and the reward 246. In particular, after the user's determination of compliance and the level of compliance, in certain embodiments the monitoring system determines a reward to the user of the PUA 244 and/or communicates a message to the user indicating the user's compliance, level of compliance and/or the reward to the user 246. These actions are similar to those described above with respect to FIG. 3A, and also to 108 and 110 described above with respect to FIG. 2A and to 206 and 208 described above with respect to FIG. 2B. Accordingly, a detailed description thereof is unnecessary.

Figure 4:
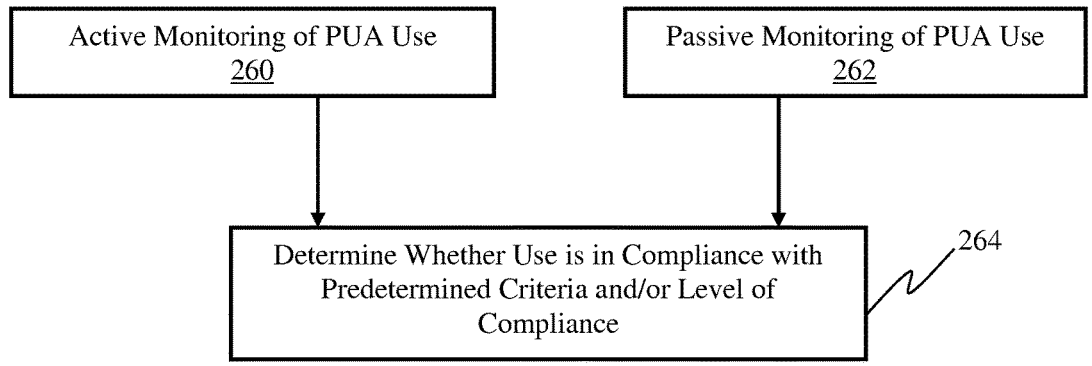
FIG. 4 is a flow diagram illustrating actions by the monitoring systems of FIGS. 1A-1C which actively and passively monitor use of the PUA.

In certain embodiments described herein, the methods and systems for monitoring use of a research device in accordance with at least one predetermined use criterion comprise actively monitoring use of the research device by the user by communicating a message to the user requesting a response and passively monitoring use of the research device by the user by sensing at least one parameter indicating whether the research device is being used in accordance with the at least one predetermined criterion. FIG. 4 illustrates the actions performed by the monitoring system in these embodiments where the research device comprises a PUA. In other embodiments, the monitoring system monitors the use of a research device that does not comprise a PUA.

As shown in FIG. 4, the monitoring system actively and passively monitors the use of the PUA. Active monitoring 260 of the PUA use includes requesting an action by the user to show compliance with at least one predetermined use criterion and, in particular, comprises communicating a request message to the user requesting a response to the request message. Such active monitoring is similar to the actions 100, 102 and 104 of the monitoring system described with respect to FIGS. 2A and 2B herein above, and detailed descriptions thereof are unnecessary.

Unlike active monitoring 260, passive monitoring 262 does not request any specific action to be performed by the user so as to indicate compliance with the PUA use criteria, and comprises sensing or detecting one or more parameters that indicate whether the PUA is being used in compliance with at least one predetermined criterion. Referring to FIG. 1B, the sensing or detecting is performed in the PUA 2 by the sensor/detector 13, and includes, but is not limited to, one or more of sensing a biometric parameter of the user, detecting a presence indication signal or a personal identification signal, sensing external sounds, detecting location of the PUA, detecting location change of the PUA, detecting motion of the PUA, detecting data input, sensing pressure applied to the PUA, detecting recharging, power capacity and/or docking of the PUA and detecting impact of the PUA with another object. These passive monitoring activities are similar to those described herein above with respect to FIGS. 3A and 3B, and therefore detailed description thereof is unnecessary.

Referring to FIG. 4, the monitoring system determines whether the use of the PUA is in compliance with at least one predetermined criterion and/or the level of the user's compliance 264 based on the active 260 and passive 262 monitoring of the PUA use. In particular, the active monitoring 260 and the passive monitoring 262 provide data which is used to determine whether the PUA is being used in compliance with at least one predetermined criteria and/or the level of the user's compliance 264. As discussed above, the compliance and/or level of compliance determination indicates one or more of whether the PUA is being carried and/or used, whether the PUA is charged, whether the PUA has been recharged and/or docked, whether the PUA is being carried and/or used by a specific user, whether the PUA is "on", whether the PUA is working properly, whether the PUA is being carried and whether or not by a particular user and whether the PUA 2 is capable of collecting, storing and/or communicating research data, or of cooperating with one or more other devices to do so. In certain embodiments, the monitoring system notifies the user, after the compliance determination in 264, of the user's compliance or non-compliance and/or the user's level of compliance with the predetermined criteria by communicating a message to the user. In some embodiments, the monitoring system also determines a reward to the user based on the user's compliance and/or level of compliance, and communicates to the user a message indicating the reward. These actions are described in more detail herein above with respect to FIGS. 2A-3B, and detailed descriptions thereof are therefore omitted. It is understood that, as in the embodiments of FIGS. 2A-3B, the determination of the reward and communication of a message to the user indicating compliance, level of compliance and/or reward are optional.

In certain embodiments, the PUA carries out passive monitoring to produce passively monitored data, the monitoring system communicates a request message to the PUA, the PUA automatically produces a response including and/or based on the passively monitored data and communicates the response to the monitoring system and the monitoring system determines whether the use of the PUA complies with at least one predetermined use criterion based on the passively monitored data. In certain ones of such embodiments, the PUA communicates its response at a time when the PUA is to be carried in accordance with a predetermined schedule. In certain ones of such embodiments, the monitoring system communicates the request at a time when the PUA is to be carried in accordance with a predetermined schedule.

In certain embodiments, compliant use of a research device by a user is promoted by producing compliance data for a plurality of different times and/or time periods, indicating whether the research device is being used in compliance with at least one predetermined use criterion, producing level data, representing a level of compliance by the user, and communicating a message to the user indicating a level of compliance of the user based on the level data. These embodiments are illustrated in FIG. 5 in connection with the use of a PUA, but it will be appreciated that these embodiments are also applicable where the research device does not comprise a PUA.

Figure 5:
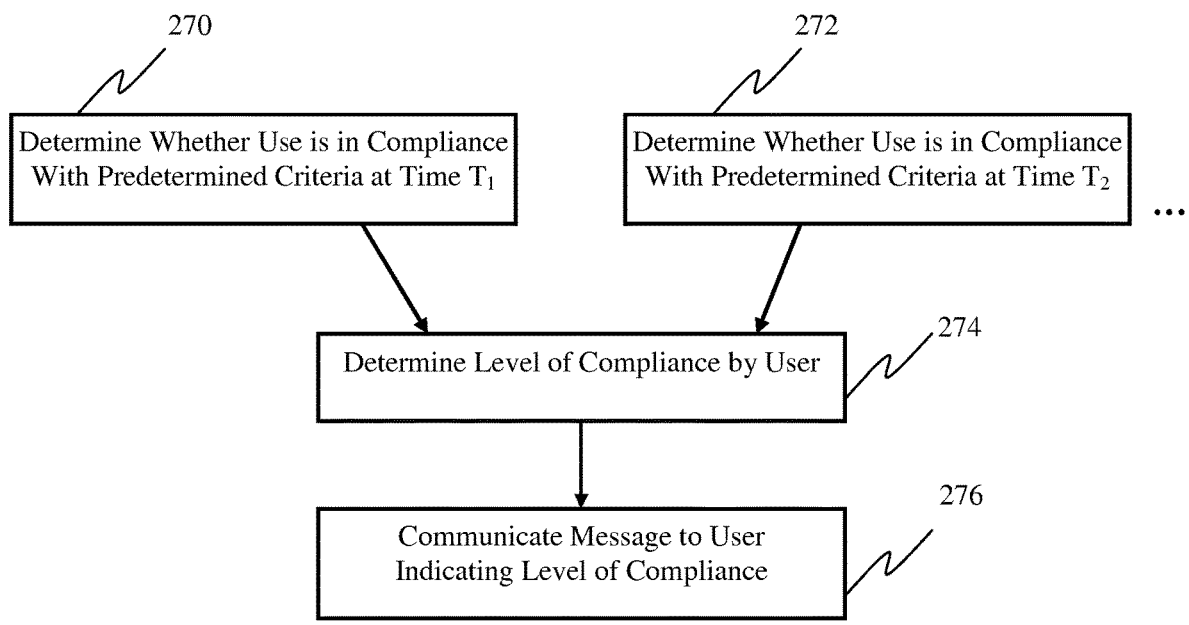
FIG. 5 is a flow diagram illustrating actions by the monitoring systems of FIGS. 1A-1C which determine compliance for a plurality of different times.

As shown in FIG. 5, the monitoring system determines whether use of the PUA is in compliance with at least one predetermined criterion at least at a first time 270, i.e. at time $T_1$, (or for a selected time period) and thereafter determines whether used of the PUA is in compliance with the at least one predetermined criterion at least at a second time 272, i.e. at time $T_2$ (or for a selected time period). These compliance determinations are based on at least one of the active monitoring and the passive monitoring described herein above with respect to FIGS. 2A-4. It is understood that the number of compliance determinations is not limited to two and that the monitoring system can perform such determinations of compliance at times $T_1$ through $T_n$, where n is any predetermined number, or for any desired number of time periods. These determinations are performed at pre-selected time intervals, at pre-selected times of the day and/or at random times. In certain embodiments the monitoring system sends messages according to a schedule to the PUA requesting data from which compliance can be assessed. In certain ones of such embodiments the schedule is produced using a pseudorandom sequence of times and dates. In certain ones of such embodiments, the schedule is produced to ensure that messages are sent during predetermined time periods during the day, such as during selected dayparts.

The plurality of compliance determinations 270, 272 by the monitoring system provide compliance data which indicates whether the PUA is being used in accordance with the at least one predetermined use criterion. Referring now to FIG. 1B, the compliance data is provided by the PUA and/or by the processor 5 of the monitoring system 1.

Referring back to FIG. 5, the monitoring system determines 274 the level of compliance by the user based on the compliance data produced in the plurality of compliance determinations 270 and 272. The determination of the user's level of compliance is performed by the PUA 2 or the processor 5 of the monitoring system 1 of FIG. 1B, using the compliance data to determine to what extent the user has complied with at least one predetermined use criterion. As a result of the level of compliance determination, level data indicating the level of compliance by the user is provided.

After the level of the user's compliance is determined, the monitoring system communicates a message to the user indicating the level of compliance 276. The message to the user is generated in the PUA 2 or by the processor 5 of the system based on the level data produced by the monitoring system in 274. In certain embodiments, where the message is generated by the processor 5, the message is communicated to the user through communications 7. As mentioned above, the message can be in the form of a text message, a voice mail, a voice message, an e-mail, a web page, a telephone call, an image, or any other indication of the level of compliance to the user. The message can be communicated to the user using the output of the PUA such as, for example, by displaying the message on a display screen thereof or by playing the message using a speaker or earphone thereof. Alternatively, the message can be communicated to the user using any other suitable device.

Communication of a message to the user indicating compliance with the use requirements and/or the user's level of compliance promotes correct use of the PUA by keeping the user informed as to whether or not his or her use is in compliance with the use requirements. In this way, the user can compare his or her level of compliance from one time to another and try to improve the level of compliance over time.

In certain embodiments, the monitoring system promotes use of research devices by a plurality of users in compliance with at least one predetermined use criterion by producing level data representing relative compliance levels of each of a plurality of research device users and communicating a message to each of the plurality of users indicating the user's compliance relative to others of the plurality of research device users. In certain ones of such embodiments, the level data comprises comparative compliance rank data that indicates the user's compliance rank or level compared with the compliance rank or level of the other research device users of the plurality of users. The determination of each user's comparative compliance rank or level is performed by the processor 5 of the monitoring system 1 of FIG. 1B which processes data relating to compliance and/or level of compliance and provides level data indicating the selected user's relative compliance level in comparison with the compliance level of other research device users.

In certain embodiments, the level data represents the user's compliance rank or level relative to the compliance ranks or levels of all other research device users monitored by the monitoring system. In certain other embodiments, the research device users may be divided into a plurality of user groups, with each user belonging to at least one user group. Each user group is determined based on common users' characteristics such as age, sex, income, profession, location, preferences and/or interests, family relationships, and other characteristics. In such embodiments, the level data produced by the monitoring system represents the user's compliance rank or level compared with the compliance ranks or levels of other users within the same group. Thus, for example, research device users can be divided into user groups that include members of the same household, and the level data provided by the monitoring system indicates the user's relative level of compliance related to the levels of compliance of other users in the same household.

Based on the level data produced by the monitoring system, a message is generated and communicated to each user. The message to each user indicates the user's compliance level relative to others of the plurality of the research device users. The message may be in the form of a text message, a voicemail, a voice message, an image, a telephone call, an e-mail, a web page, a paper message or any other suitable message that is capable of informing the user of the user's relative compliance. In the monitoring system of FIG. 1B, the message is generated by the processor 5 and can be communicated to each user via the communication 7. The message can be communicated either directly to the user, such as by a telephone call, text message, e-mail or the like, to the research device of the user or to any other suitable device or by any other suitable means. The communication of the message to each user indicating the user's relative compliance promotes competition among the users, and among the members of the user group, e.g. of the same household, where the research device users are divided into a plurality of groups as discussed above.

This, in turn, promotes use of the research devices in compliance with the predetermined use requirements by each of the users.

In certain embodiments, data concerning usage of a PUA to perform a user-beneficial function is gathered by the monitoring system. In particular, the gathering of data concerning such usage of the PUA comprises monitoring usage of the PUA to produce usage data within the PUA, and communicating the usage data from the PUA to a usage data processing facility. This embodiment is illustratively shown in FIG. 6. This is especially useful for gathering marketing data concerning how users employ PUA's with an ability to communicate, such as cellular telephones, PDA's, notebook and laptop computers, Blackberry devices, PCS devices, two-way radios, as well as other kinds of PUA's having device-to-device communicating ability or wireless networking ability.

Figure 6:
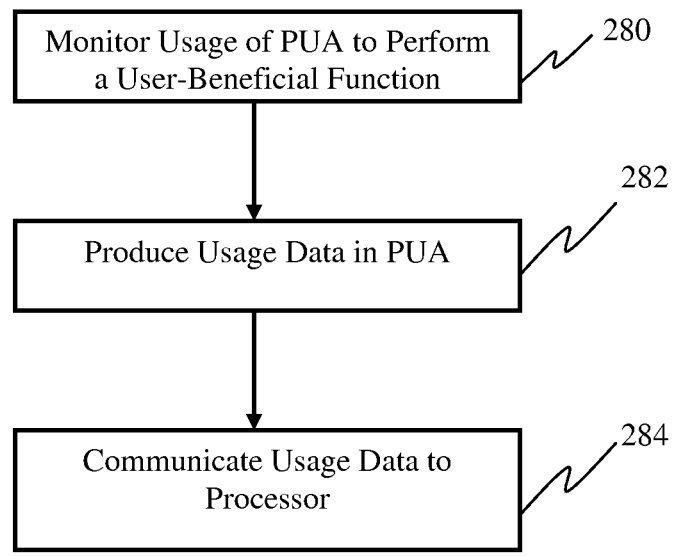
FIG. 6 is a flow diagram illustrating actions by the monitoring systems of FIGS. 1A-1C which monitor usage of the PUA.

As shown in FIG. 6, the monitoring system monitors the user's use of the PUA 280 and produces usage data within the PUA 282 based on such monitoring. If the monitoring system shown in FIG. 1B is employed, certain monitoring of PUA usage is performed by the sensor/detector 13, which detects the use of one or more functions performed by the PUA. For example, if the PUA includes a function of generating and communicating a text message to another PUA, the sensor/detector 13 in the PUA 2 detects when the user generates and/or communicates a text message, and usage data relating to the generation and communication of the text message is produced in the PUA 2. In certain ones of these embodiments, the operations of sensor/detector 13 are implemented by a processor of the PUA that may carry out additional operations beyond those of sensor/detector 13.

The usage data produced in the PUA 2 includes at least one of data indicating the type of PUA function used, data indicating the time of use of the PUA function, data indicating the length of time of the use of the PUA function, data relating to the use of communications, if any, to send or receive messages with the use of the PUA and data relating to content, if any, generated by the performance of the PUA function. Data relating to the use of communications by the PUA includes data relating to the time a message is communicated, the size of the message and/or the destination of the message, such as the recipient's telephone number, email address and/or IP address. Data relating to the content generated by the use of the PUA function includes data relating to the subject of the generated content and/or data relating to words, phrases, names or concepts included in the content, such as "buzz words". Buzz words comprise words, terms or phrases that advertisers and other businesses would find of value as descriptive of consumers' experiences and reactions to media and advertising content. Some examples include word pair choices such as " boring" vs. "exciting"; "essential" vs. "un-necessary." Further examples include words and phrases that convey a rank-order (ordinal) scale such as "superior quality" vs. "good quality" vs. "acceptable" vs. "poor quality" vs. "unacceptable," "not interested at all" vs. "slightly interested" vs. "might consider purchasing" vs. "interested in purchasing" vs. "plan to purchase" vs. "will definitely purchase."

The usage data produced in the PUA is thereafter communicated 284 to a usage data processing facility. The usage data processing facility includes a processor, such as the processor 5 shown in FIG. 1B. The processing facility is adapted to receive and process usage data to generate trend data relating to a variety of trends. The trend data generated by the processing facility includes, but is not limited to, data relating to the time, frequency and/or manner of usage of the PUA function, the preference of one PUA function over others, the use of a particular "buzz word," name, brand and/or concept by users, the communications to a particular area code, IP address and/or email service, and other trends relating to the usage of the PUA.

In certain embodiments, the PUA includes communications for communicating with at least another PUA, and the methods and systems for monitoring use of a PUA comprise detecting communicating a message by the communications of the PUA, providing monitored data relating to the message, and providing trend data representing at least one trend of usage of the PUA by the user based on the monitored data. These embodiments are illustrated in FIG. 7 which shows a flow diagram of actions performed by the monitoring system.

In this embodiment, the PUA is adapted to communicate with other PUA's using a communication interface. As shown in FIG. 1B, the PUA 2 includes communications in the form of an interface 9 which can communicate using the communications 7. In this case, each of the other PUA's also includes a corresponding interface which is coupled with the communications 7, such that each such PUA can communicate with other PUA's via the communications 7.

Figure 7:
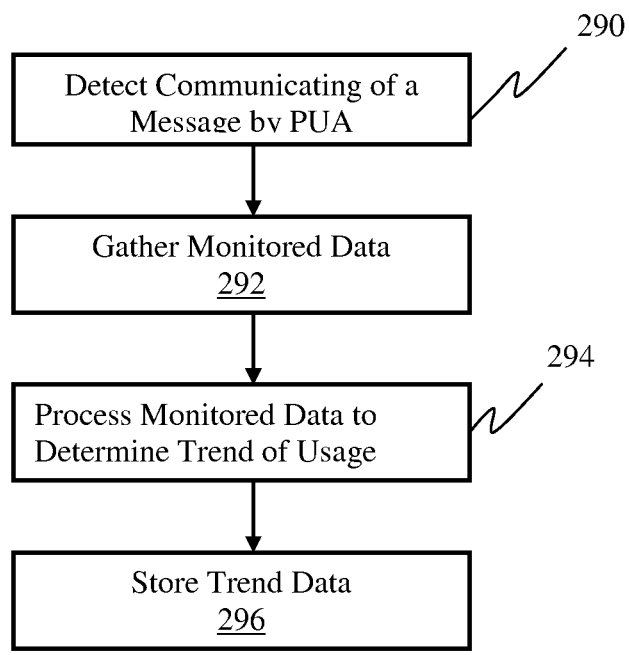
FIG. 7 is a flow diagram illustrating actions by the monitoring systems of FIGS. 1A-1C which provide trend data representing one or more PUA usage trends.

Referring now to FIG. 7, when the interface of the PUA communicates a message with another PUA or with any other device, the communicating of the message is detected 290 in the PUA. If the PUA 2 shown in FIG. 1B is employed, the sensor/detector 13 is used to detect the communicating of the message by the PUA 2. In certain ones of such embodiments, the operation of sensor/detector 13 is provided by a processor that may carry out operations in addition to those of sensor/detector 13. In certain embodiments, the communicating by the PUA is detected by detecting a connection between the interface of the PUA with another PUA or device. In other embodiments, the communicating by the PUA is detected by detecting data sent from or received by the interface.

When communicating of the message by the PUA is detected, monitored data relating thereto is gathered 292. In particular, the monitored data includes data related to one or more of the time of communicating, the duration of communicating, the length or size of the message, the type of message (e.g., e-mail, voice, text message, etc.), the source and/or the recipient of the message, and the content of the message, such as the subject of the communication and/or the use of pre-selected words, names, concepts or images in the communication. The monitored data is then processed 294 to determine at least one trend of usage of the PUA by the user and to provide trend data relating to at least one trend of usage. If the monitoring system 1 of FIG. 1B is used, the monitored data is processed either in the PUA 2, or is first communicated to the processor 5 via the communications 5 and thereafter processed by the processor 5 to provide trend data. Trend data provided based on the monitored data comprises data relating to at least one of the PUA functions used by the user, the type of messages sent or received by the user, the frequency of messages sent or received by the user, the time of communicating the messages, the duration of the communicating, the source and recipient of the messages and the content of the messages.

The trend data provided by the monitoring system is then stored 296 either in the PUA or in an external storage. In the monitoring system 1 of FIG. 1B, the trend data is stored in at least one of the PUA 2 or in the storage 6. If the trend data is stored in the PUA 2, this data can thereafter be communicated to an external storage device such as the storage 6 of the monitoring system 1.

Trend data provided in the embodiments shown in FIGS. 6 and 7, and described above, can be used as market research data to determine user preferences, including the user's preferences relating to the PUA functions. Thus, for example, trend data can be used to determine which functions of the PUA are most frequently used by which users, which functions could be removed or added in future versions of the PUA products. In the embodiments in which trend data includes data related to the content of PUA users' communications, trend data can be used to determine the popularity or success of a particular product, brand, person or concept and to ascertain how well a particular product, service or brand may do in the market.

Figure 8:
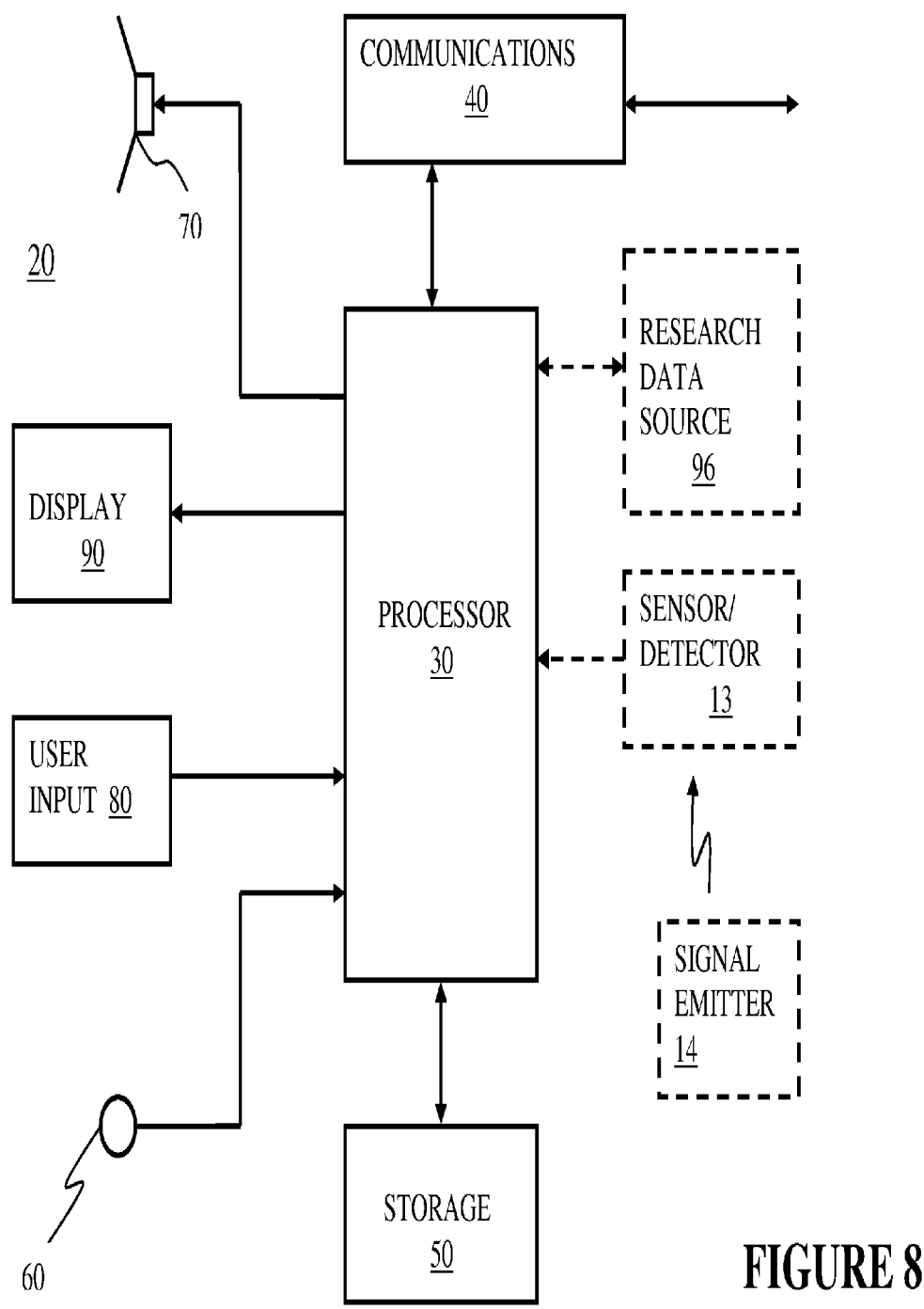
FIG. 8 is a block diagram of a cellular telephone configured to operate as a research device.

FIG. 8 is a block diagram of a cellular telephone 20 modified to carry out a research operation. The cellular telephone 20 comprises a processor 30 that is operative to exercise overall control and to process audio and other data for transmission or reception and communications 40 coupled to the processor 30 and operative under the control of processor 30 to perform those functions required for establishing and maintaining a two-way wireless communication link with a respective cell of a cellular telephone network. In certain embodiments, processor 30 also is operative to execute applications ancillary or unrelated to the conduct of cellular telephone communications, such as applications serving to download audio and/or video data to be reproduced by cellular telephone 20, e-mail clients and applications enabling the user to play games using the cellular telephone 20. In certain embodiments, processor 30 comprises two or more processing devices, such as a first processing device (such as a digital signal processor) that processes audio, and a second processing device that exercises overall control over operation of the cellular telephone 20. In certain embodiments, processor 30 employs a single processing device. In certain embodiments, some or all of the functions of processor 30 are implemented by hardwired circuitry.

Cellular telephone 20 further comprises storage 50 coupled with processor 30 and operative to store data as needed. In certain embodiments, storage 50 comprises a single storage device, while in others it comprises multiple storage devices. In certain embodiments, a single device implements certain functions of both processor 30 and storage 50.

In addition, cellular telephone 20 comprises a microphone 60 coupled with processor 30 to transduce the user's voice to an electrical signal which it supplies to processor 30 for encoding, and a speaker and/or earphone 70 coupled with processor 30 to convert received audio from processor 30 to an acoustic output to be heard by the user. Cellular telephone 20 also includes a user input 80 coupled with processor 30, such as a keypad, to enter telephone numbers and other control data, as well as a display 90 coupled with processor 30 to provide data visually to the user under the control of processor 30.

In certain embodiments, the cellular telephone 20 provides additional functions and/or comprises additional elements. In certain ones of such embodiments, the cellular telephone 20 provides e-mail, text messaging and/or web access through its wireless communications capabilities, providing access to media and other content. For example, Internet access by the cellular telephone 20 enables access to video and/or audio content that can be reproduced by the cellular telephone for the user, such as songs, video on demand, video clips and streaming media. In certain embodiments, storage 50 stores software providing audio and/or video downloading and reproducing functionality, such as iPod® software, enabling the user to reproduce audio and/or video content downloaded from a source, such as a personal computer via communications 40 or through Internet access via communications 40.

To enable cellular telephone 20 to gather research data, namely, data indicating exposure to audio such as programs, music and advertisements, research software is installed in storage 50 to control processor 30 to gather such data and communicate it via communications 40 to a research organization. The research software in certain embodiments also controls processor 30 to store the data for subsequent communication.

In certain embodiments, the research software controls the processor 30 to decode ancillary codes in the transduced audio from microphone 60 using one or more of the known techniques described hereinabove, and then to store and/or communicate the decoded data for use as research data indicating encoded audio to which the user was exposed. In certain embodiments, the research software controls the processor 30 to extract a signature from the transduced audio from microphone 60 using one or more of the known techniques identified hereinabove, and then to store and/or communicate the extracted signature data for use as research data to be matched with reference signatures representing known audio to detect the audio to which the user was exposed. In certain embodiments, the research software both decodes ancillary codes in the transduced audio and extracts signatures therefrom for identifying the audio to which the user was exposed. In certain embodiments, the research software controls the processor 30 to store samples of the transduced audio, either in compressed or uncompressed form for subsequent processing either to decode ancillary codes therein or to extract signatures therefrom. In certain ones of these embodiments, the compressed or uncompressed audio is communicated to a remote processor for decoding and/or signature extraction.

Where the cellular telephone 20 possesses functionality to download and/or reproduce presentation data, in certain embodiments, research data concerning the usage and/or exposure to such presentation data as well as audio data received acoustically by microphone 60, is gathered by cellular telephone 20 in accordance with the technique illustrated by the functional block diagram of FIG. 8A. Storage 50 of FIG. 8 implements an audio buffer 54 for audio data gathered with the use of microphone 60. In certain ones of these embodiments storage 50 implements a buffer 56 for presentation data downloaded and/or reproduced by cellular telephone 20 to which the user is exposed via speaker and/or earphone 70 or display 90, or by means of a device coupled with cellular telephone 20 to receive the data therefrom to present it to a user. In some of such embodiments, the reproduced data is obtained from downloaded data, such as songs, web pages or audio/video data (e.g., movies, television programs, video clips). In some of such embodiments, the reproduced data is provided from a device such as a broadcast or satellite radio receiver of the cellular telephone 20 (not shown for purposes of simplicity and clarity). In certain ones of these embodiments storage 50 implements a buffer 56 for metadata of presentation data reproduced by cellular telephone 20 to which the user is exposed via speaker and/or earphone 70 or display 90, or by means of a device coupled with cellular telephone 20 to receive the data therefrom to present it to a user. Such metadata can be, for example, a URL from which the presentation data was obtained, channel tuning data, program identification data, an identification of a prerecorded file from which the data was reproduced, or any data that identifies and/or characterizes the presentation data, or a source thereof. Where buffer 56 stores audio data, buffers 54 and 56 store their audio data (either in the time domain or the frequency domain) independently of one another. Where buffer 56 stores metadata of audio data, buffer 54 stores its audio data (either in the time domain or the frequency domain) and buffer 56 stores its metadata, each independently of the other.

Processor 30 separately produces research data 58 from the contents of each of buffers 54 and 56 which it stores in storage 50. In certain ones of these embodiments, one or both of buffers 54 and 56 is/are implemented as circular buffers storing a predetermined amount of audio data representing a most recent time interval thereof as received by microphone 60 and/or reproduced by speaker and/or earphone 70, or downloaded by cellular telephone 20 for reproduction by a different device coupled with cellular telephone 20. Processor 30 extracts signatures and/or decodes ancillary codes in the buffered audio data to produce research data. Where metadata is received in buffer 56, in certain embodiments the metadata is used, in whole or in part, as research data 58, or processed to produce research data 58. The research data is thus gathered representing exposure and/or usage of audio data by the user where audio data is received in acoustic form by the cellular telephone 20 and where presentation data is received in non-acoustic form (for example, as a cellular telephone communication, as an electrical signal via a cable from a personal computer or other device, as a broadcast or satellite signal or otherwise).

In certain embodiments, the cellular telephone 20 is provided with a research data source 96 coupled by a wired or wireless coupling with processor 30 for use in gathering further or alternative research data to be communicated to a research organization. In certain ones of these embodiments, the research data source 96 comprises a location data producing device or function providing data indicating a location of the cellular telephone 20. Various devices appropriate for use as source 96 include a satellite location signal receiver, a terrestrial location signal receiver, a wireless networking device that receives location data from a network, an inertial location monitoring device and a location data producing service provided by a cellular telephone service provider. In certain embodiments, research data source 96 comprises a device or function for monitoring exposure to print media, for determining whether the user is at home or out of home, for monitoring exposure to products, exposure to displays (such as outdoor advertising), presence within or near commercial establishments, or for gathering research data (such as consumer attitude, preference or opinion data) through the administration of a survey to the user of the cellular telephone 20. In certain embodiments, research data source 96 comprises one or more devices for receiving, sensing or detecting data useful in implementing one or more of the foregoing functions, other research data gathering functions and/or for producing data ancillary to functions of gathering, storing and/or communicating research data, such as data indicating whether the panelist has complied with predetermined rules governing the activity or an extent of such compliance. Such devices include, but are not limited to, motion detectors, accelerometers, temperature detectors, proximity detectors, satellite positioning signal receivers, video cameras, image scanners using visible or infra-red light or other radiant energy, chemical sensors, digital writing tablets, blood flow sensors, pulse oximeters, pulse monitors, RFID readers, RF receivers, wireless networking transceivers, wireless device coupling transceivers, pressure detectors, deformation detectors, electric field sensors, magnetic field sensors, optical sensors, electrodes (such as EEG and/or EKG electrodes), audio sensors, and the like. In certain embodiments, such devices are supplied in cellular telephones to provide a user-beneficial function, so that their capabilities can also be employed to gather research data and/or to gather data indicating whether the panelist has complied with predetermined use criteria. Such devices include but are not limited to, microphones, video cameras and satellite positioning signal receivers.

In certain embodiments dedicated devices are included in or with the cellular telephone 20 to gather data for assessing compliance, such as sensor/detector 13 described above in connection with FIGS. 1B, 3A and 3B. In certain ones of such embodiments, sensor/detector 13 comprises a digital writing tablet that is used to input a digital handwritten signature from the user to assess whether the cellular telephone 20 is being carried by the correct person. In accordance with known handwriting identification techniques, storage 50 stores signature recognition software to control processor 30 to compare the current user's signature input by means of the digital writing tablet against a stored template of the correct user's handwritten signature to determine if there is a match. Based on the results of the matching process, data is produced indicating whether the current user's signature matches the signature represented by the stored template to assess whether the current user of the cellular telephone 20 is the same as the panelist who has agreed to carry and use cellular telephone 20 to gather research data. The template of the panelist's signature is produced in a training mode of the signature recognition software, in which the panelist inputs one or more signatures using the digital writing tablet from which the template is produced by processor 30 and then stored in storage 50. In certain ones of such embodiments, the cellular telephone 20 includes a digital writing tablet to enable a user-beneficial function, such as note taking and it is then unnecessary to provide a dedicated digital writing tablet as the sensor/detector 13.

In certain ones of such embodiments, a voiceprint recognition technique is used to assess whether the cellular telephone 20 is being carried by the correct person. In accordance with known voiceprint recognition techniques, storage 50 stores voice recognition software to control processor 30 to compare the current user's voice input by means of the microphone 60 against a stored voiceprint of the correct user's voice to determine if there is a match. Based on the results of the matching process, data is produced indicating whether the current user's voice matches the voice represented by the stored voiceprint to assess whether the current user of the cellular telephone 20 is the same as the panelist who has agreed to carry and use cellular telephone 20 to gather research data. The voiceprint of the panelist's voice is produced in a training mode of the voice recognition software, in which the panelist speaks into microphone 20 to produce data from which the voiceprint is produced by processor 30 and then stored in storage 50. Various ones of such embodiments extract the user's voiceprint under different conditions. In one such embodiment, the user's voiceprint is extracted when the user places a voice call using the cellular telephone in response to a request message from a monitoring system. In other such embodiments, the processor 30 extracts voiceprints continuously from the output of microphone 60, or at predetermined times or intervals, or when a telephone call is made using cellular telephone 20 or when the output from microphone 60 indicates that someone may be speaking into it (indicated, for example by the magnitude of the output, and/or its time and/or frequency characteristics). The extracted voiceprints are compared to the stored voiceprint to assess whether the correct person is using the cellular telephone 20.

In certain ones of such embodiments, sensor/detector 13 comprises an imagining device, such as a video camera, or other radiant energy detector, such as a line scanner implemented by means of a CCD or an array of photodiodes, that is used to input data representing an image or line scan of a physical feature of the user, such as an iris, a retina, an image of all or portion of the user's face, finger, palm, hand or ear to assess whether the cellular telephone 20 is being carried by the correct person. In the case of an iris or retinal image, the input data is processed to extract an iris or retinal pattern code. A facial image is processed to extract data unique to the user such as a signature or feature set representing facial bone structure. An image of a finger, palm or hand is processed to extract a fingerprint or palm print, or other characteristic data such as hand geometry or tissue vascular structure. In accordance with known pattern recognition techniques, storage 50 stores pattern recognition software to control processor 30 to compare the current user's iris or retinal pattern code, facial signature or feature set or other characteristic data input by means of the sensor/detector 13 against a stored pattern code, signature, feature set or other characteristic data of the correct user, as the case may be, to determine if there is a match. Such characteristic data may be stored in storage 50 or in a storage of a separate device, system or processing facility. Based on the results of the matching process, data is produced by processor 30 operating under control of the pattern recognition software to assess whether the current user of the cellular telephone 20 is the same as the panelist who has agreed to carry and use cellular telephone 20 to gather research data. The pattern code, signature, feature set or other characteristic data of the correct user is produced in a training mode of the pattern recognition software, in which the appropriate physical feature of the panelist is imaged or scanned one or more times using the sensor/detector 13 from which the desired data is produced by processor 30 and then stored in storage 50. In certain embodiments the physical feature concerned is scanned or imaged at a plurality of different orientations to produce the desired data. In certain ones of the foregoing embodiments, the cellular telephone 20 includes a digital camera to enable a user-beneficial function, such as digital photography or video imaging and it is then unnecessary to provide a dedicated imaging device or scanner as the sensor/detector 13.

In certain ones of such embodiments where user input 80 comprises one or more keys, a keyboard dynamics technique is used to assess whether the cellular telephone 20 is being used by the correct person. In accordance with known keyboard dynamics techniques, storage 50 stores keystroke monitoring software to control processor 30 to collect characteristic keystroke parameters, such as data indicating how long the user holds down the keys of input 80, the delay between one keystroke and the next (known as "latency"), and frequency of using of special keys, such as a delete key. Still other parameters, such as typing speed and the manner in which the user employs key combinations (such as keyboard shortcuts), may be monitored by processor 30. These parameters are processed in a known manner to produce a feature set characterizing the user's key usage style which is then compared against a stored feature set representing the style of the correct user. Based on the results of this comparison, data is produced indicating whether the current user's key usage style matches that of the correct user as represented by the stored feature set to assess whether the current user of the cellular telephone 20 is the same as the panelist who has agreed to carry and use cellular telephone 20 to gather research data. The feature set representing the usage style of the panelist is produced in a training mode of the software, in which the panelist makes use of the key or keys of user input 80 to produce data from which the feature set is produced by processor 30 and then stored in storage 50.

In certain ones of such embodiments, sensor/detector 13 comprises a motion sensitive device, such as an accelerometer, that produces data related to motion of the cellular telephone 20. This data is used to produce a feature set characterizing motion of the cellular telephone 20, and thus the gait of the person carrying the cellular telephone. In accordance with known gait identification techniques, storage 50 stores pattern recognition software to control processor 30 to compare the current user's gait feature set against a stored reference feature set representing the gait of the correct user to determine if there is a match. Based on the results of the matching process, data is produced indicating whether the current user's gait matches the gait represented by the stored feature set to assess whether the current user of the cellular telephone 20 is the same as the panelist who has agreed to carry and use cellular telephone 20 to gather research data. The feature set of the panelist's gait is produced in a training mode of the pattern recognition software, in which the panelist walks about carrying the cellular telephone 20 while the sensor/detector 13 produces data from which processor 30 produces a reference feature set which it stores in storage 50. In certain ones of such embodiments, the cellular telephone 20 includes an accelerometer as an input device to enable a user-beneficial function, such as a gaming input or scrolling command input, and it is then unnecessary to provide a dedicated accelerometer as the sensor/detector 13.

In certain ones of such embodiments, multiple devices and pattern recognition techniques are employed to produce a more accurate and reliable identification of the user than is possible using only one such pattern recognition technique. In certain embodiments, one or more of such pattern recognition techniques or other passive data gathering technique is employed to assess when cellular telephone 20 possibly is not in the possession of the correct user. Such detection may be based on an amount by which a monitored feature set differs from a stored feature set representing a characteristic of the correct user as determined by processor 30. When the processor 30 produces data indicating that the cellular telephone 20 might not be in the possession of the correct user, in certain embodiments either processor 30 controls a speaker, earphone or visual display of the cellular telephone 20 to present a message to the user requesting a response from which the user's identity as the correct user or as a different person may be determined, or processor 30 sends a message via communications 40 to a monitoring system indicating that such a message should be presented to the user. In the latter case, the monitoring system responds to such message from the processor 30 to send a message to the cellular telephone 20 for presentation to the user to request an appropriate response from the user from which the user's identity as the correct user or someone else may be determined, either by processor 30 or by the monitoring system. The user's response to such message is used to determine whether the actual user is the correct user.

In certain embodiments, sensor/detector 13 comprises a device appropriate for receiving a presence indication signal or a personal identification signal from signal emitter 14 worn or carried by the user or implanted in the user. In such embodiments, sensor/detector 13 comprises an appropriate one of an RF receiver, a microphone, an optical sensor, an inductive pickup, a capacitive pickup, a chemical sensor or a conductive connection.

Figure 9A:
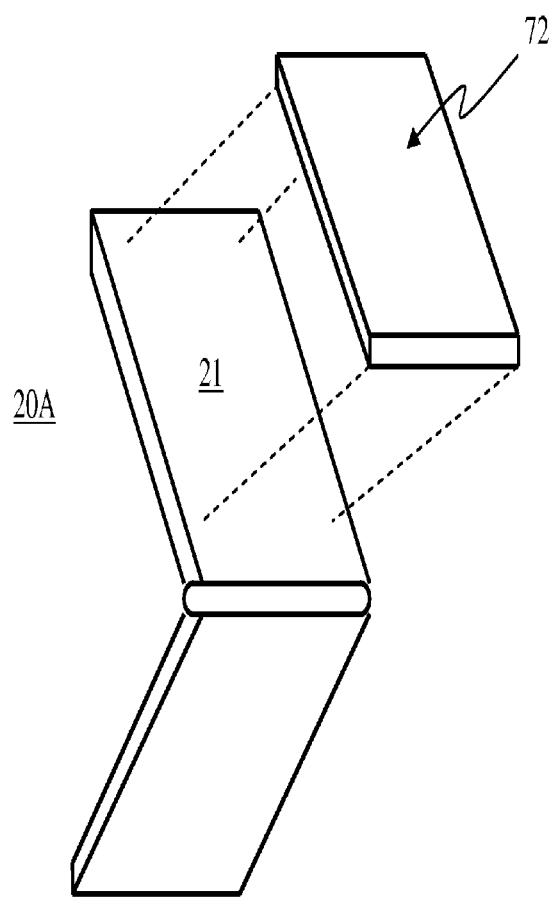
FIG. 9A is an exploded view of a cellular telephone with a research data monitor affixed thereto.
Figure 9B:
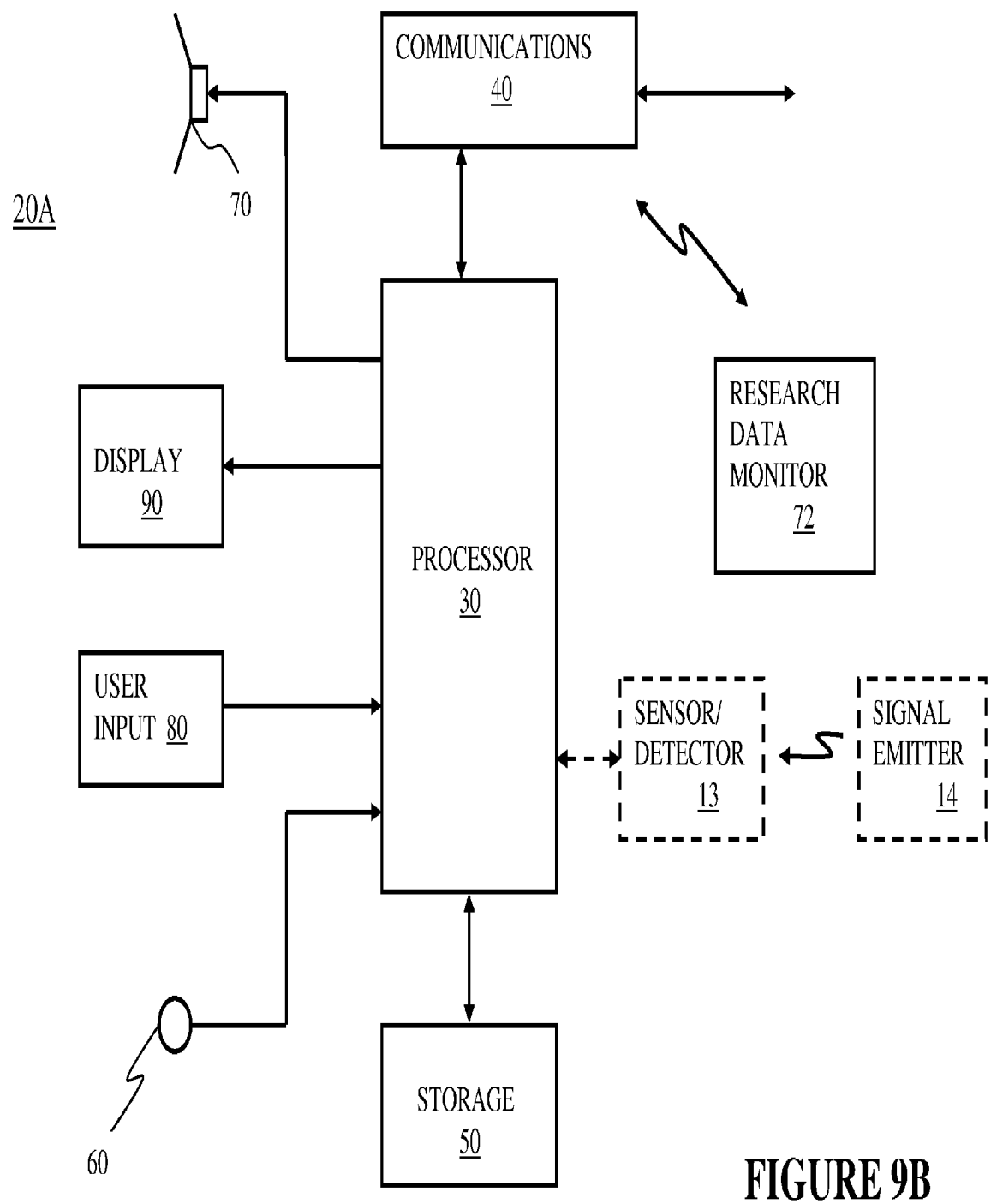
FIG. 9B is a block diagram illustrating the cellular telephone of FIG. 9A coupled with the research data monitor thereof.

FIG. 9A illustrates a research data monitor 72 affixed to an outer surface 21 of a cellular telephone 20A, wherein the monitor 72 is operative to gather research data and communicate it to cellular telephone 20A which in turn communicates the research data to a monitoring system. Cellular telephone 20A is illustrated in the block diagram of FIG. 9B. As shown in FIG. 9B, cellular telephone 20a comprises the same elements as cellular telephone 20 of FIG. 8, except that research data source 96 is omitted from the embodiment of FIG. 2B.

Figure 9C:
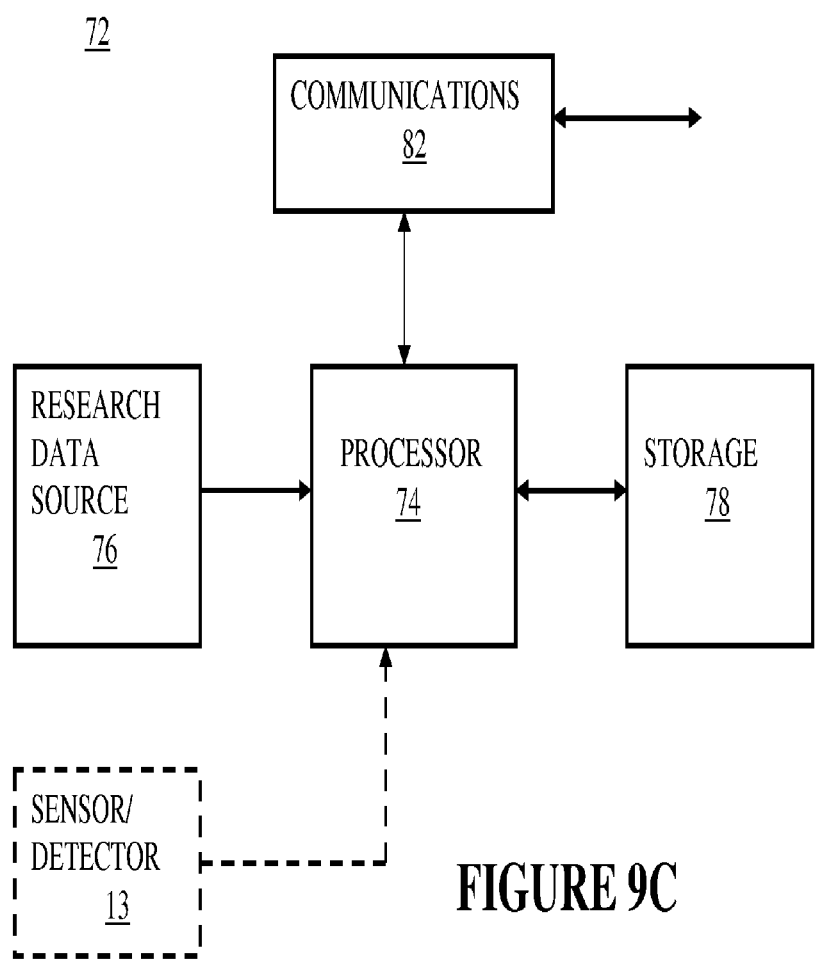
FIG. 9C is a block diagram of the research data monitor of FIGS. 9A and 9B.

Research data monitor 72 is illustrated in the block diagram of FIG. 9C. The research data monitor 72 comprises a processor 74 that is operative to exercise overall control of the monitor 72 and to process data for transmission or reception and communications 82 coupled to the processor 74 and operative under the control of processor 74 to perform those functions required for conducting communications with cellular telephone 20A. In certain embodiments, processor 74 comprises two or more processing devices, such as a first processing device (such as a digital signal processor) that processes research data, such as audio data, and a second processing device that exercises overall control over operation of the monitor 72. In certain embodiments, processor 74 employs a single processing device. In certain embodiments, some or all of the functions of processor 74 are implemented by software, while in other embodiments, the functions of processor 74 are implemented in hardwired circuitry without the use of software.

In certain embodiments, communications 82 establishes and maintains a wireless communication link with communications 40 of cellular telephone 20A, using a Bluetooth™ protocol, a ZigBee™ protocol, an inductive link, a capacitive link, an RF link, infrared link, or otherwise. In certain embodiments, communications 82 communicates with communications 40 using a wired link, such as a USB interface, a Firewire® interface, a connection to a plug or jack of the cellular telephone 20A or an internal connection to cellular telephone 20A.

Research data monitor 72 further comprises a research data source 76 coupled with processor 74. In certain embodiments, research data monitor 72 comprises a microphone that serves to transduce acoustic energy for processing by processor 74 to produce research data. In certain embodiments, research data source 76 comprises a keypad that enables the user to input data, such as channel or station data, user identification data or another kind of research data. In certain embodiments, monitor 72 comprises an RF receiver and/or infrared radiation detector. In certain embodiments, monitor 72 comprises a sensor/detector 13 of the kind described hereinabove in connections with FIGS. 1B, 3A, 3B and/or 8a and/or a location data producing device or function providing data indicating a location of the monitor 72, which can serve also to produce research data. Various devices appropriate for use as sensor/detector 13 include a satellite location signal receiver, a terrestrial location signal receiver, a wireless networking device that receives location data from a network, an inertial location monitoring device and a location data producing service provided by a cellular telephone service provider. In certain embodiments, sensor/detector 13 comprises a device appropriate for receiving a presence indication signal or a personal identification signal from signal emitter 14 worn or carried by the user or implanted in the user. In such embodiments, sensor/detector 13 comprises an appropriate one of an RF receiver, a microphone, an optical sensor, an inductive pickup, a capacitive pickup, a chemical sensor or a conductive connection.

In certain embodiments, monitor 76 comprises a device or function for monitoring exposure to print media, for determining whether the user is at home or out of home, for monitoring exposure to products, exposure to displays (such as outdoor advertising), presence within or near commercial establishments, or for gathering research data (such as consumer attitude, preference or opinion data) through the administration of a survey to the user of the cellular telephone 20A. In certain embodiments, monitor 76 comprises one or more devices for receiving, sensing or detecting data useful in implementing one or more of the foregoing functions, other research data gathering functions and/or for producing data ancillary to functions of gathering, storing and/or communicating research data, such as data indicating whether the panelist has complied with predetermined rules governing the activity or an extent of such compliance. Such devices include, but are not limited to, motion detectors, accelerometers, temperature detectors, proximity detectors, satellite positioning signal receivers, RFID readers, RF receivers, wireless networking transceivers, wireless device coupling transceivers, pressure detectors, deformation detectors, electric field sensors, magnetic field sensors, chemical sensors, optical sensors, electrodes, and the like.

Monitor 72 further comprises storage 78 coupled with processor 74 and operative to store data as needed. In certain embodiments, storage 78 comprises a single storage device, while in others it comprises multiple storage devices. In certain embodiments, a single device implements certain functions of both processor 74 and storage 78.

Figure 9D:
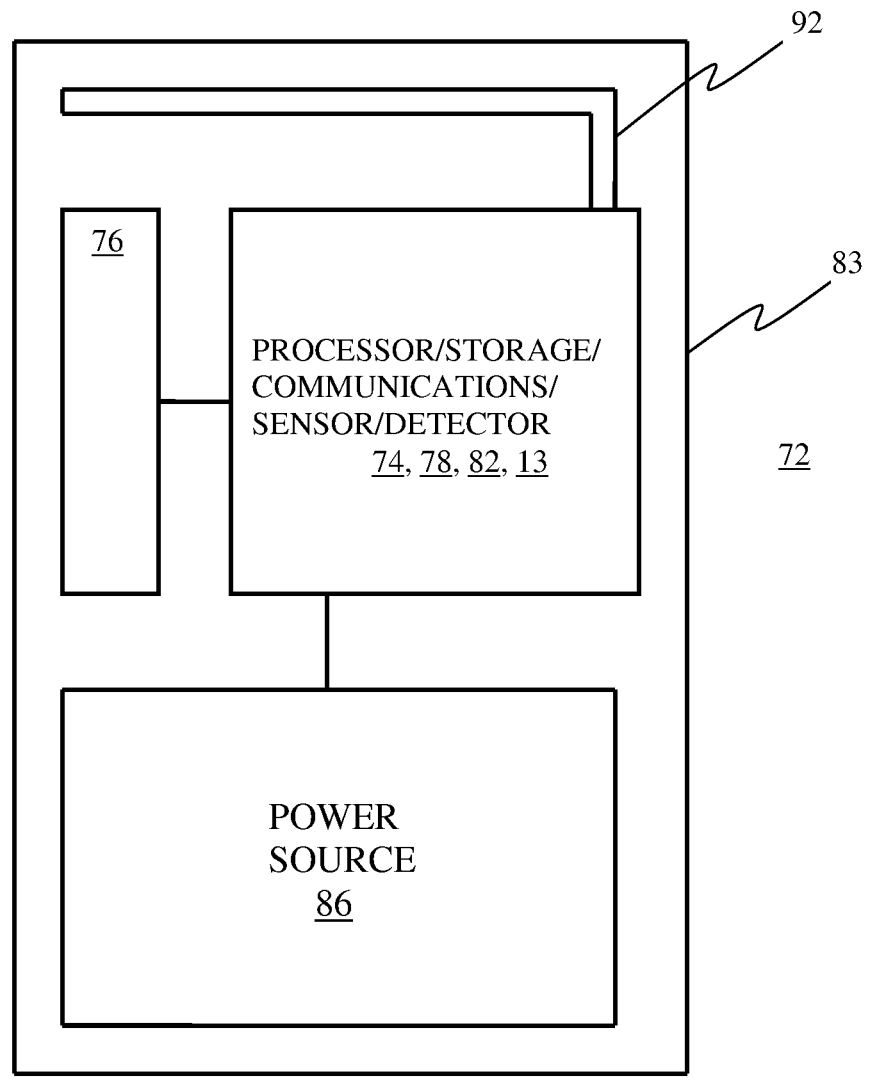
FIG. 9D is a layout diagram of an embodiment of the research data monitor of FIGS. 9A, 9B and 9C.

FIG. 9D illustrates an embodiment of research data monitor 72 fabricated on a substrate 83, such as a printed circuit board or a flexible substrate comprising paper, plastic or the like, on which certain elements of monitor 72 are printed on substrate 83. Power source 86 comprises a battery (either rechargeable or non-rechargeable) or a charge storage device such as a capacitor, printed on substrate 83. In the embodiment of FIG. 9D, communications 82 comprises an RF transceiver, such as a Bluetooth™ transceiver, a ZigBee™ transceiver or other RF transceiver. An antenna 92 is printed on substrate 83 and coupled with communications 82. It will be appreciated that monitor 72 can be fabricated to have a very thin profile and very low weight, so that it may be affixed to the enclosure of a cellular telephone, a PDA or other PUA that is carried on the person of a participant, without adding substantially to its size or weight.

Although various embodiments of the present invention have been described with reference to a particular arrangement of parts, features and the like, these are not intended to exhaust all possible arrangements or features, and indeed many other embodiments, modifications and variations will be ascertainable to those of skill in the art.

What is claimed is:

1. A method for monitoring use by a user of a portable research device in accordance with at least one predetermined use criterion comprising:
passively gathering gait data for assessing an identity of the user of the portable research device, the portable research device including an accelerometer, the passively gathered gait data obtained from the accelerometer;
determining, via a processer communicatively coupled to the portable research device, gait assessment data based on the passively gathered gait data, the gait assessment data indicating a possibility that the user is not a predetermined user of the portable research device, the processor remote from the portable research device;
based on the gait assessment data, displaying a first message to the user requesting a response from which the user's identity is determined; and
determining, via the processor, whether the user is the predetermined user based on a response to the first message.

2. The method of claim 1, further including employing pattern recognition techniques to assess when the portable research device is not in the possession of the predetermined user.

3. The method of claim 1, further including controlling a speaker or an earphone of the portable research device to present the first message to the user requesting a response from which the user's identity as the predetermined user or as a different person may be determined.

4. The method of claim 1, further including sending a second message via communications to a monitoring system indicating that the first message should be presented to the user.

5. The method of claim 1, further including determining whether use of the portable research device complies with at least one predetermined use criterion and/or a level of compliance therewith based on monitoring data and the response to the first message.

6. The method of claim 5, further including producing the monitoring data by monitoring at least one of the user's heart activity, the user's breathing activity, the user's borborygmus (gastrointestinal noise), the user's vascular pattern, the user's facial and/or ear patterns, the user's fingerprint and/or handprint, and the user's retinal and/or iris pattern.

7. The method of claim 6, further including determining at least one of a first level, a second level, or a third level of the user's compliance with use of the portable research device based on i) the monitored data and ii) the user's compliance with the predetermined use criterion.

8. The method of claim 7, further including obtaining research data indicative of exposure of the portable research device to media based on determining that the user's compliance is associated with the first level.

9. A system for monitoring use by a user of a portable research device in accordance with at least one predetermined use criterion comprising:
a memory; and
instructions;
a processor to be programmed by the instructions to:
passively gather gait data for assessing an identity of the user of the portable research device, the portable research device including an accelerometer, the passively gathered data received from the accelerometer;
determine, via the processor, gait assessment data based on the passively gathered gait data, the gait assessment data indicating a possibility that the user is not a predetermined user of the portable research device, the processor communicatively coupled to the portable research device, the processor remote from the portable research device;
based on the gait assessment data, display a first message to the user requesting a response from which the user's identity is determined; and
determine whether the user is the predetermined user based on a response to the first message.

10. The system of claim 9, wherein the processor is to employ pattern recognition techniques to assess when the portable research device is not in the possession of the predetermined user.

11. The system of claim 9, wherein the processor is to control a speaker or an earphone of the portable research device to present the first message to the user requesting a response from which the user's identity as the predetermined user or as a different person may be determined.

12. The system of claim 9, wherein the processor is to send a second message via communications to a monitoring system indicating that the first message should be presented to the user.

13. The system of claim 9, further including the processor to determine whether use of the portable research device complies with at least one predetermined use criterion and/or a level of compliance therewith based on monitoring data and the response to the first message.

14. The system of claim 13, further including the processor to:
produce the monitoring data by monitoring at least one of the user's heart activity, the user's breathing activity, the user's borborygmus (gastrointestinal noise), the user's vascular pattern, the user's facial and/or ear patterns, the user's fingerprint and/or handprint, and the user's retinal and/or iris pattern;
determine at least one of a first level, a second level, or a third level of the user's compliance with use of the portable research device based on i) the monitored data and ii) the user's compliance with the predetermined use criterion; and
obtain research data indicative of exposure of the portable research device to media based on determining that the user's compliance is associated with the first level.

15. A non-transitory machine readable storage device comprising instructions that, when executed, cause a machine to at least:
passively gather gait data for assessing an identity of a user of a portable research device the portable research device including an accelerometer, the passively gathered gait data received from the accelerometer;
determine, via a processor communicatively coupled to the portable research device, gait assessment data based on the passively gathered gait data, the gait assessment data indicating a possibility that the user is not a predetermined user of the portable research device, the processor remote from the portable research device;
based on the gait assessment data, display a first message to the user requesting a response from which the user's identity is determined; and
determine, via the processor, whether the user is the predetermined user based on a response to the first message.

16. The non-transitory machine readable storage device of claim 15, wherein the instructions, when executed, further cause the machine to employ pattern recognition techniques to assess when the portable research device is not in the possession of the predetermined user.

17. The non-transitory machine readable storage device of claim 15, wherein the instructions, when executed, further cause the machine to control a speaker or an earphone of the portable research device to present the first message to the user requesting a response from which the user's identity as the predetermined user or as a different person may be determined.

18. The non-transitory machine readable storage device of claim 15, wherein the instructions, when executed, further cause the machine to send a second message via communications to a monitoring system indicating that the first message should be presented to the user.

19. The non-transitory machine readable storage device of claim 15, wherein the instructions, when executed, further cause the machine to determine whether use of the portable research device complies with at least one predetermined use criterion and/or a level of compliance therewith based on monitoring data and the response to the message.

20. The non-transitory machine readable storage device of claim 19, wherein the instructions, when executed, further cause the machine to:
produce the monitoring data by monitoring at least one of the user's heart activity, the user's breathing activity, the user's borborygmus (gastrointestinal noise), the user's vascular pattern, the user's facial and/or ear patterns, the user's fingerprint and/or handprint, and the user's retinal and/or iris pattern;
determine at least one of a first level, a second level, or a third level of the user's compliance with use of the portable research device based on i) the monitored data and ii) the user's compliance with the predetermined use criterion; and
obtain research data indicative of exposure of the portable research device to media based on determining that the user's compliance is associated with the first level.

* * * * *